(12) United States Patent
Kuo et al.

(10) Patent No.: US 11,357,788 B2
(45) Date of Patent: Jun. 14, 2022

(54) NUCLEAR PARASPECKLE ASSEMBLY TRANSCRIPT 1 AS THERAPEUTIC TARGETING IN NEURODEGENERATION

(71) Applicant: ACADEMIA SINICA, Taipei (TW)

(72) Inventors: Hung-Chih Kuo, Taipei (TW); Yi-Ying Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 74 days.

(21) Appl. No.: 16/355,545

(22) Filed: Mar. 15, 2019

(65) Prior Publication Data

US 2019/0282605 A1 Sep. 19, 2019

Related U.S. Application Data

(60) Provisional application No. 62/643,568, filed on Mar. 15, 2018.

(51) Int. Cl.
*A61K 31/7105* (2006.01)
*A61P 25/16* (2006.01)
*A61P 25/28* (2006.01)

(52) U.S. Cl.
CPC .......... *A61K 31/7105* (2013.01); *A61P 25/16* (2018.01); *A61P 25/28* (2018.01)

(58) Field of Classification Search
None
See application file for complete search history.

(56) References Cited

U.S. PATENT DOCUMENTS

2017/0037408 A1* 2/2017 Chakravarty ........ C12N 15/113

FOREIGN PATENT DOCUMENTS

WO 2014177867 A2 11/2014

OTHER PUBLICATIONS de Boer et al. J. Neurol. Neurosurg. Psychiatry 2021;vol. 92, pp. 86-95.*
Sunwoo et al. Mol. Neurobiol. 2017, vol. 54, pp. 1577-1586.*
Lagier-Tourenne, C. and D.W. Cleveland, "Rethinking ALS: the FUS about TDP-43." Cell, 2009.136(6): p. 1001-1004.
Paez-Colasante, X., et al., "Amyotrophic lateral sclerosis: mechanisms and therapeutics in the epigenomic era." Nat Rev Neurol, 2015. 11(5): p. 266-279.
Shimonaka, S., et al., "Templated Aggregation of TAR DNA-binding Protein of 43 kDa (TDP-43) by Seeding with TDP-43 Peptide Fibrils." J Biol Chem, 2016. 291(17): p. 8896-8907.
Ryan, V.H., et al., "Mechanistic View of hnRNPA2 Low-Complexity Domain Structure, Interactions, and Phase Separation Altered by Mutation and Arginine Methylation." Mol Cell, 2018. 69(3): p. 465-479 e7.
Lourenco, G.F., et al., "Long noncoding RNAs in TDP-43 and FUS/TLS-related frontotemporal lobar degeneration (FTLD)." Neurobiol Dis, 2015. 82: p. 445-454.
Errichelli, L., et al., "FUS affects circular RNA expression in murine embryonic stem cell-derived motor neurons." Nat Commun, 2017. 8:14741, 11 pages.
Brettschneider, J., et al., "Stages of pTDP-43 pathology in amyotrophic lateral sclerosis." Ann Neurol, 2013. 74(1): p. 20-38.
Tollervey, J.R., et al., "Characterizing the RNA targets and position-dependent splicing regulation by TDP-43." Nat Neurosci, 2 011. 14(4): p. 452-458.
Neumann, M., et al., "Ubiquitinated TDP-43 in frontotemporal lobar degeneration and amyotrophic lateral sclerosis." Science, 2006. 314(5796): p. 130-133.
Huang, Y.C., et al., "Inhibition of TDP-43 aggregation by nucleic acid binding." PLoS One, 2013. 8(5): e64002, 11 pages.
Search Report in Taiwan Counterpart Application No. 108109003, dated Aug. 14, 2020, in 1 page; English translation provided.
Tomohiro Yamazaki et al., "The building process of the functional paraspeckle with long non-coding RNAs." Front Biosci (Elite Ed). Jan. 1, 2015;7:1-47.

* cited by examiner

*Primary Examiner* — Tracy Vivlemore
(74) *Attorney, Agent, or Firm* — Duane Morris LLP

(57) ABSTRACT

The present disclosure provides a method of reducing neurodegeneration and/or TDP43 associated aggregation, comprising knocking down the expression of Nuclear Paraspeckle Assembly Transcript 1 (NEAT1) or LncRNA NEAT1. Also provided are methods for screening a candidate agent that reduces neurodegeneration and/or TDP43 associated aggregation in a cell, treating or preventing a neurodegenerative disorder, delaying or preventing the onset of a neurodegenerative disorder or reducing a risk for developing a neurodegenerative disorder in a subject and determining whether a subject is suffering from, or at a risk of developing a neurodegenerative disorder, comprising measuring the presence of cytoplasmic NEAT1 in a biological sample, wherein the presence is indicative of the risk of developing a neurodegenerative disorder.

10 Claims, 31 Drawing Sheets
(25 of 31 Drawing Sheet(s) Filed in Color)
Specification includes a Sequence Listing.

FIG. 1A
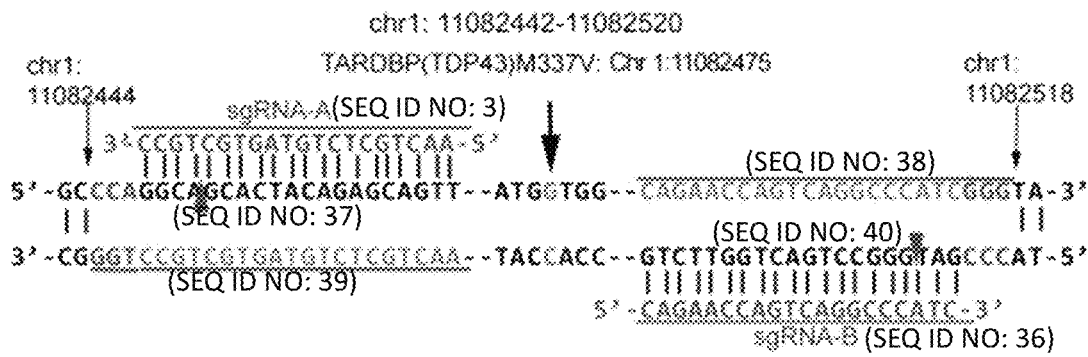
FIG. 1B
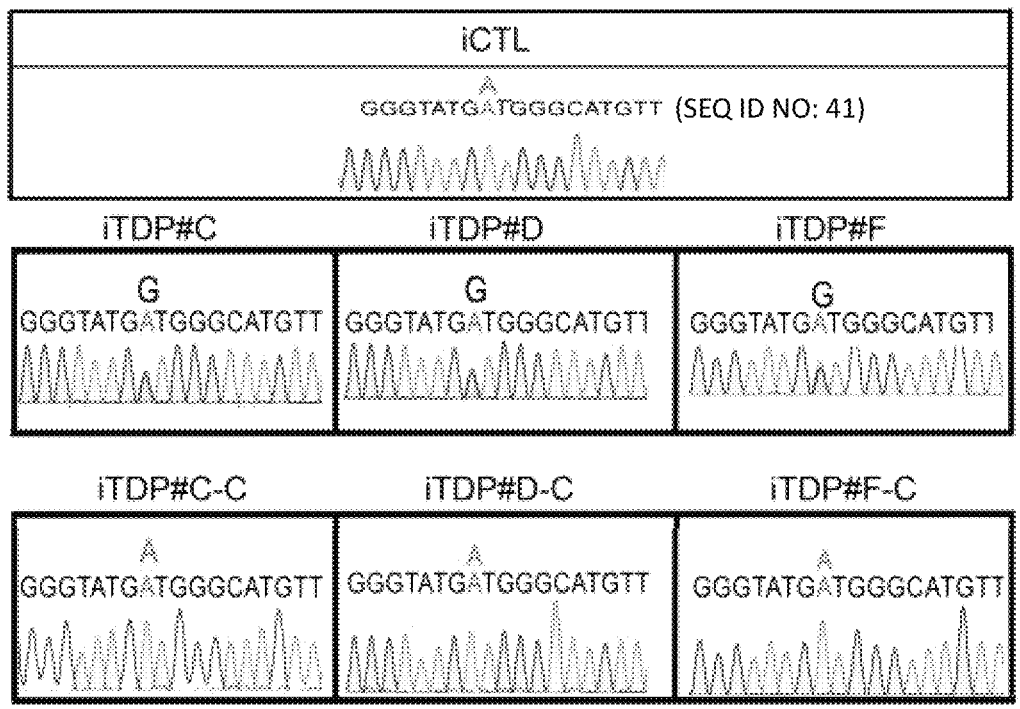
FIG. 1C

NUCLEAR PARASPECKLE ASSEMBLY TRANSCRIPT 1 AS THERAPEUTIC TARGETING IN NEURODEGENERATION

CROSS-REFERENCE TO RELATED APPLICATIONS

This application claims priority to U.S. Prov. App. No. 62/643,568 filed Mar. 15, 2018 entitled "NUCLEAR PARASPECKLE ASSEMBLY TRANSCRIPT 1 AS THERAPEUTIC TARGETING IN NEURODEGENERATION", which are each incorporated by reference in its entirety.

The instant application contains a Sequence Listing which has been submitted electronically in ASCII format and is hereby incorporated by reference in its entirety. Said ASCII copy, created on Sep. 25, 2020, is named US8677_ST25.txt and is 7,122 bytes in size. In connection with the Sequence Listing submitted concurrently herewith, the applicant hereby states that the content of the electronically filed submission is in accordance with 37 C.F.R. § 1.821(e); and the submission, in accordance with 37 C.F.R. § 1.821(g), does not include new matter.

FIELD OF THE INVENTION

The present invention relates in general to the field of gene knockdown of in reduction of neurodegeneration. Particularly, the present invention relates to the development of methods for treating and/or preventing a neurodegenerative disorder by knocking down Nuclear Paraspeckle Assembly Transcript 1 (NEAT1) and methods for screening candidate of reducing neurodegeneration and/or TDP43 associated aggregation and/or treating and/or preventing a neurodegenerative disorder.

BACKGROUND OF THE INVENTION

Amyotrophic lateral sclerosis (ALS) is an adult onset neurodegenerative disorder caused by progressive loss of motor neurons (MNs) in the brain, brain stem and spinal cord. The pathological mechanisms proposed for ALS are still unknown, but alteration of microenvironment of motor neurons is caused by protein aggregation, RNA processing, metal imbalance, oxidative stress, glutamate excitotoxicity, mitochondria dysfunction, glial dysfunction, neuroinflammation, apoptosis, and fragmental Golgi apparatus. For the past decades, the devastating motor neuron disease ALS has been intensively studied for discovering causes and developing cures. Transgenic rodent models have been generated for studying disease pathogenesis and developing therapeutic drugs. Although there are several drugs available, the effects are still limited. Therefore, there is an urgent need to unravel this complexity for potential therapeutic strategies.

Current ALS modeling systems for drug development are not sufficient for drug development. Lack of access to patient motor neurons has held back drug development for ALS. Human pluripotent stem cells (hPSCs) have been used for benefit in human development as well as disease modeling. Thus, human inducible pluripotent stem cells (iPSCs) will overcome the drawback and provides a remarkable potential in medicine and offer added the knowledge in ALS. Several issues of in vitro cell induction have hampered ALS disease modeling. There are some technological challenges in reprogramming. The capabilities of recapitulated ALS-disease phenotypes are inconsistent between research groups and cellular batches due to variable cell population. To eliminate variability, lineage-specific reporters provide real-time observation for cell-lineage tracing and downstream analysis. Conventional reporters have been extensively exploited for monitoring transcriptional regulation; however, a lack of chromatin complex and regulatory elements has constrained the studies of transcriptional machinery. Genome editing provides a tool for targeting specific gene locus in vivo through double strand breaks followed by homologous recombination. Precise targeting has improved by using paired guide RNAs and double nicking mediated by CRISPR-Cas9. Genetic correction of disease mutations have been established and rescued disease phenotypes in β-haemoglobinopathy, Parkinson's diseases and Duchenne muscular dystrophy. In ALS modeling systems, the genetic mutations of superoxide dismutase 1 (SOD1) and fused in sarcoma (FUS) have been corrected to identify novel disease pathogenesis for immense therapeutic potential.

The common pathological hallmark of ALS is TDP-43 proteinopathy, and cytoplasmic TDP43 inclusions are coupled to striking loss of nuclear TDP43. This proteinopathy was also found in other neurodegenerative disease including TDP-43 positive frontotemporal lobar degeneration (FTLD) and Alzheimer's disease (AD) (Lagier-Tourenne, C. and D. W. Cleveland, *Rethinking ALS: the FUS about TDP-43. Cell,* 2009. 136(6): p. 1001-4). TAR DNA binding protein 43 (TDP-43; MIM*605078; 43 kDa; chromosome 1 p36.2) is a nuclear RNA binding protein shuttling between nucleus and cytoplasm involving in transcription, RNA metabolism and processing. The pathological role of TDP-43 is still unknown; however, cytoplasmic TDP43 accumulation and aggregation has been proposed to be the underlying mechanism of cellular dysfunction and death in this group of disorders (Paez-Colasante, X., et al., *Amyotrophic lateral sclerosis: mechanisms and therapeutics in the epigenomic era. Nat Rev Neurol,* 2015. 11(5): p. 266-79).

In consideration of understanding the pathogenesis of TDP43, the pathways involved in TDP43 nucleocytoplasmic transport have been explored and disrupted in ALS patient brain tissues with C9orf72 hexanucleotide repeats expansion (GGGGCC) due to physical interaction of RanGAP1. Moreover, the oligomers of TDP-43 have been detected in ALS and FTLD-TDP post-mortem sections. Therefore, understanding TDP-43 associated pathogenesis would be beneficial for early detection and drug developments (Shimonaka, S., et al., *Templated Aggregation of TAR DNA-binding Protein of* 43 *kDa (TDP-43) by Seeding with TDP-43 Peptide Fibrils. J Biol Chem,* 2016. 291(17): p. 8896-907). Untangling TDP43 aggregation has become one of the major focuses for developing ALS therapeutic treatment. Recently, several cell-free systems have been established for exploring aggregation of RNA binding proteins with low complexity domains including TDP43, FUS and so on (Ryan, V. H., et al., *Mechanistic View of hnRNPA2 Low-Complexity Domain Structure, Interactions, and Phase Separation Altered by Mutation and Arginine Methylation. Mol Cell,* 2018. 69(3): p. 465-479 e7). So far, TDP43 self-seeding has been well-established and confirmed in cell systems. Both detergent resistant aggregates and cleaved TDP43 can promote TDP43 aggregation/inclusion, fibrillation and promote further cell death (Shimonaka, S., et al., *Templated Aggregation of TAR DNA-binding Protein of* 43 *kDa (TDP-43) by Seeding with TDP-43 Peptide Fibrils. J Biol Chem,* 2016. 291(17): p. 8896-907). However, there is still no effective target for preventing TDP43 aggregation or mislocalization.

Advances in next generation sequencing, long noncoding RNAs (lncRNAs) have been discovered play a role in various biological functions and may be useful for disease treatments. In fact, many microRNAs and noncoding RNA have been shown associated with human diseases. Several lncRNAs have shown the potential for neurodegenerative disease including Alzheimer's disease, Parkinson's disease and multiple system atrophy (Lourenco, G. F., et al., *Long noncoding RNAs in TDP-43 and FUS/TLS-related frontotemporal lobar degeneration (FTLD). Neurobiol Dis*, 2015. 82: p. 445-54). Both ALS/FTLD-related TDP43 and FTLD-related FUS have shown interaction and regulation with lncRNAs and micro RNAs. FUS, another RNP involved in ALS, has been studied as a regulator of circRNA biogenesis (Errichelli, L., et al., *FUS affects circular RNA expression in murine embryonic stem cell-derived motor neurons. Nat Commun*, 2017. 8: p. 14741).

SUMMARY OF THE INVENTION

The present disclosure provides a method of reducing neurodegeneration and/or TDP43 associated aggregation, comprising knocking down the expression of Nuclear Paraspeckle Assembly Transcript 1 (NEAT1) or LncRNA NEAT1.

The present disclosure also provides a method of selecting a gene of interest associated with neurodegeneration and/or TDP43 associated aggregation, comprising providing iPSCs from a subject having TDP43-M337V mutation, differentiating the iPSCs to motor neuron cells, knocking out the gene of interest in the motor neuron cells, and determining the TDP43 associated aggregation in the motor neuron cells, wherein the elevated level of TDP43 associated aggregation indicates the likelihood that the gene of interest involves in neurodegeneration.

In one embodiment, gene of interest can be knocked out by clustered regularly interspaced short palindromic repeats (CRISPR) and CRISPR associated proteins (Cas) system, in which at least two vectors are used to respectively transport a Cas enzyme and RNAs that hybridize with the target sequences in genomic loci of the nucleic acid, into the cell.

The present disclosure provides a method for screening a candidate agent that reduces neurodegeneration and/or TDP43 associated aggregation in a cell, the method comprising: (a) contacting a cell with a candidate drug, and (b) assessing expression level of NEAT1 or LncRNA NEAT1 in the cell, wherein if the expression level of NEAT1 or LncRNA NEAT1 in the cell is lower than that in an untreated cell, then the candidate agent reduces neurodegeneration and/or TDP43 associated aggregation. The candidate agent has potential to treat or prevent a neurodegenerative disorder, delay or prevent the onset of a neurodegenerative disorder or reduce a risk for developing a neurodegenerative disorder.

The present disclosure also provides a method of treating or preventing a neurodegenerative disorder, delaying or preventing the onset of a neurodegenerative disorder or reducing a risk for developing a neurodegenerative disorder in a subject, comprising administering to the subject an agent that knocks down, downregulates or inhibit NEAT1 expression; or an agent inhibiting, silencing or downregulating LncRNA NEAT1.

The present disclosure also provides a method for determining whether a subject is suffering from, or at a risk of developing a neurodegenerative disorder, comprising measuring the presence of cytoplasmic NEAT1 in a biological sample, wherein the presence is indicative of the risk of developing a neurodegenerative disorder. One certain embodiment of the agent is a short nucleic acid molecule.

BRIEF DESCRIPTION OF THE DRAWING

The patent of application file contains at least one drawing executed in color. Copies of this patent or patent application publication with color drawing(s) will be provided by the Office upon request and payment of the necessary fees. FIGS. 1A to 1D shows CRISPR-Cas9 double-nicking approach for TDP43-M337V correction in iTDPs derived from three ALS-patients. FIG. 1A: Schematic shows CRISPR-Cas9n for correcting TDP43-M337V. Schematic illustrating double nicking (red arrow heads) of the human TARDBP locus. Targeting sites are labeled in blue and PAM in red. FIG. 1B: Sanger sequencing validation of TDP43-M337V correction. Representative chromatograms of TDP43-M337V in iTDP #1, iTDP #2 and iTDP #3. CRISPR-Cas9n corrected chromatograms of TDP43 denoted as iTDP #1-C, iTDP #2-C and iTDP #3-C. FIG. 1C: WGS analysis shows low gRNAs off-target effects. Summary of potential off-target locus modification in isogenic lines based on Whole genome sequencing. FIG. 1D: Characterization of iTDP #2 and iTDP #2-C by immunostaining pluripotent markers: OCT4, NANOG, TRA1-60 and SSEA4.

FIG. 2A: Representative images of TUNEL assay in MNs derived from iTDP #2 and iTDP #2-C. FIG. 2B: quantification of TUNEL+ cells in SMI32+ motor neurons. FIG. 2C: Oxygen consumption rates (OCR) in derived MNs; Relatively lower OCR in iTDP #2 and iTDP #3 derived MNs compared with iTDP #2-C and iTDP #3-C separately. ICC analysis of TDP43 mislocalization in iTDPs derived MN. Scale bar: 10 um; FIG. 2D: Representative images of TDP43 mislocalization in iTDP #2 and iTDP #2-C derived MNs. The observed Patterns of TDP43 mislocalization were labeled as N=C (TDP43 signal of nucleus=cytoplasm), N<C (TDP43 signal of nucleus<cytoplasm) and N>C (TDP43 signal of nucleus>cytoplasm). Scale bar: 10 um; FIG. 2E: Relative percentage of TDP43 mislocalization in derived MNs. FIGS. 2F and 2G: ICC analysis of TDP43 oligomers in iTDPs derived MNs. TDP43 aggregates in iTDPs derived MNs; FIG. 2H: Representative images of TDP43 aggregate in iTDP #2 and iTDP #2-C derived MNs; FIG. 2I: Relative number of TDP43 aggregates in derived MNs. Scale bar: 10 um. FIG. 2J: Quantification of TDP43-M337V caused progress of TDP43 pathology at indicated time points. FIG. 2K: Major cellular pathways altered in derived MNs between iTDP #2 v.s. iTDP #2-C and iTDP #3 v.s. iTDP #F3-C. * P<0.05, * * P<0.01, * * * P<0.001.

FIG. 3A: MN differentiation and characterization; schematic procedure of MN induction from iPSCs. SB:SB431542; LDN:LDN193189; CHIR:CHIR99021; RA: retinoic acid; PUR:Purmorphamine, AA:ascorbic acid, NFs: neurotropic factors including BDNF, GDNF, IGF1, and CNTF. BDNF: Brain-derived neurotrophic factor, GDNF: Glial cell-derived neurotrophic factor, IGF1: Insulin-like growth factor 1; CNTF: Ciliary neurotrophic factor; FIG. 3B: Representative images showing neuronal markers in derived motor neurons; FIG. 3C: The capabilities of HB9+ MN generation in iCTL1, iTDP #2, iTDP #2-C, iTDP #3, iTDP #3-C. Scale bar: 50 um. GFP Knock-in MNX1 (HB9) reporter generation; FIG. 3D: Schematic shows CRISPR-Cas9n for GFP tagging on MNX1 (HB9). Targeting sites are labelled in blue and PAM in red, and targeted allele for generating HB9-2a-GFP fusion protein; FIG. 3E: Characterization of the GFP knock-in MNs. Representative images of characterizing the GFP knock-in motor neurons by phase contrast and validation by immunostaining neuronal markers: ISL-1, HB9 and SMI32; FIG.

3F: HB9-GFP+ cells validation by immunostaining with HB9 antibodies; Scale bar: 50 um. * P<0.05, * * P<0.01, * * * P<0.001.

Figure 4A:
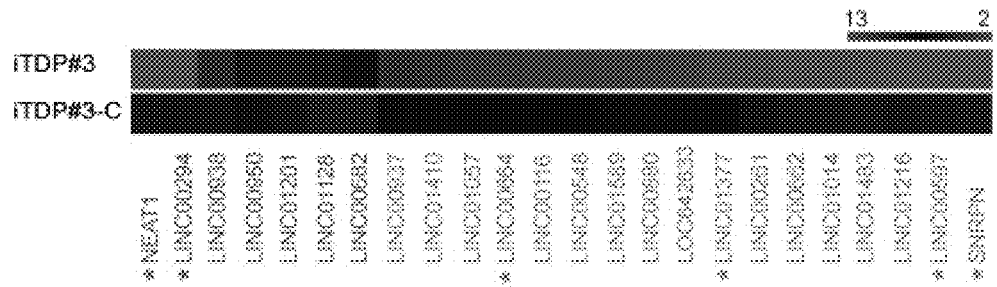
Figure 4B:
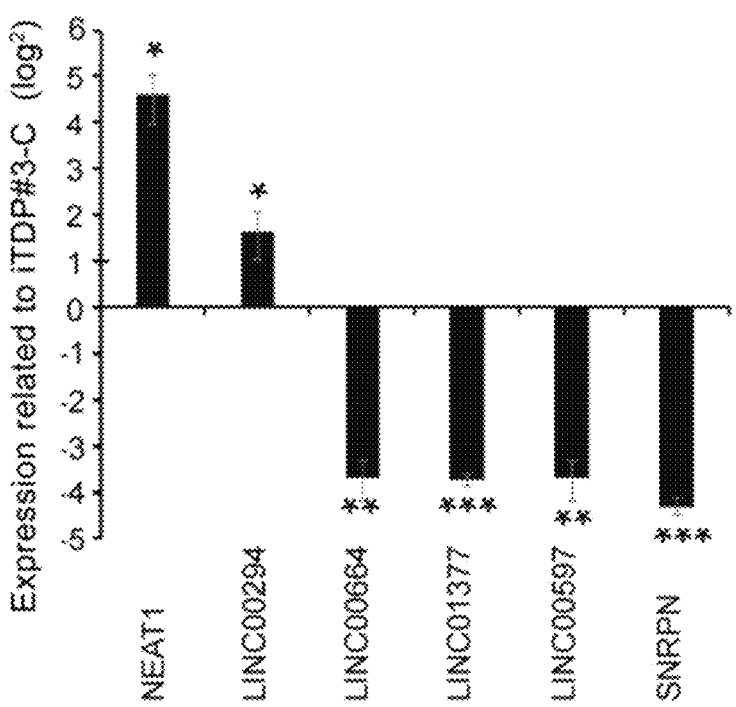
Figure 4C:
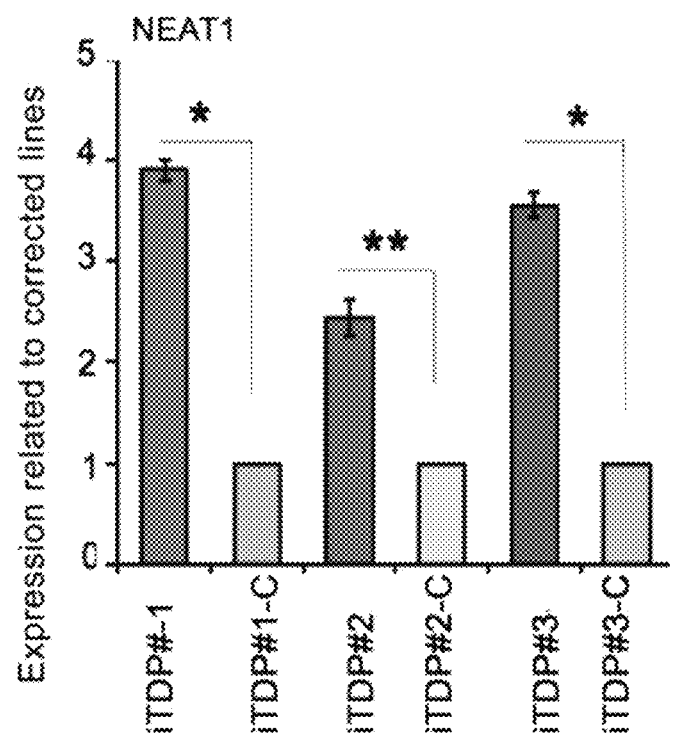
Figure 4D:
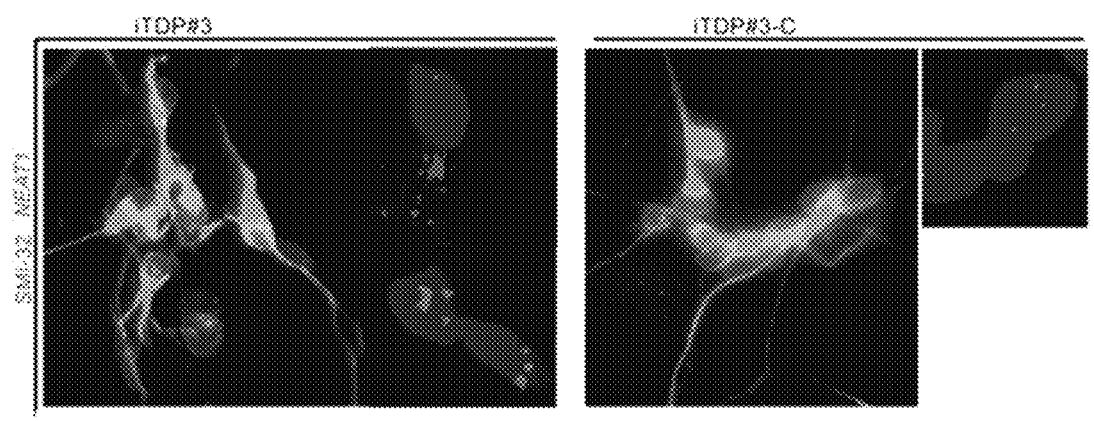
Figure 4E:
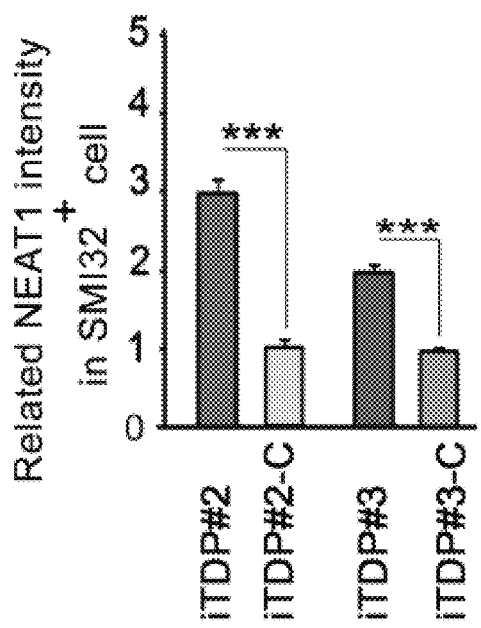
Figure 4F:
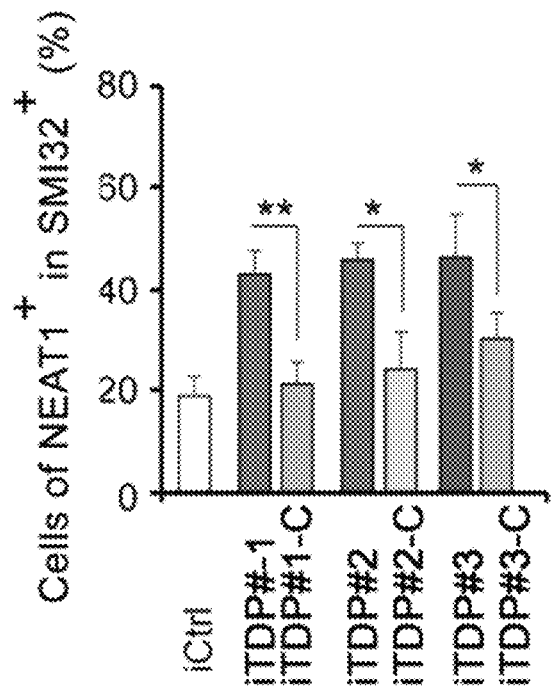
Figure 4G:
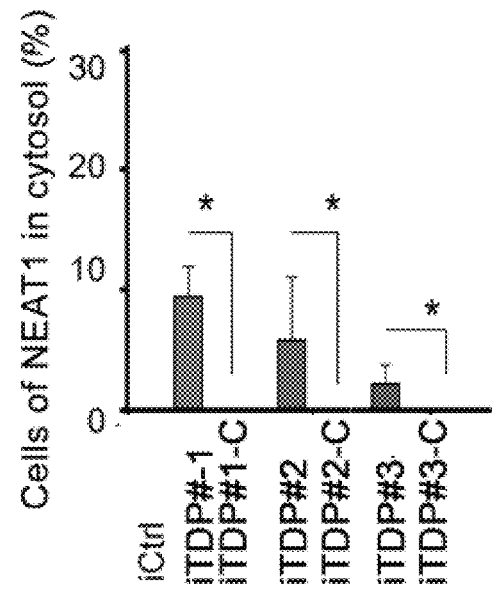

FIGS. 4A to 4G shows that LncRNA NEAT1 is upregulated and partially located in cytoplasm of iTDPs-derived MNs. Global analysis of LncRNAs expression in iTDPs-derived MNs; FIG. 4A: Heat-map of major lncRNAs expression affected in iTDP #3 v.s. iTDP #3-C; FIG. 4B: expression validation of lncRNAs by Q-PCR; FIG. 4C: Relative expression of NEAT1 in derived MNs from iTDP #1 v.s. iTDP #1-C, iTDP #2 v.s. iTDP #2-C and iTDP #3 v.s. iTDP #3-C. In situ hybridization of NEAT1 expression in cytosol of iTDPs-derived MNs; FIG. 4D: representative images of NEAT1 in derived MNs; FIG. 4E: relative intensity of NEAT1+ in MNs; FIG. 4F: percentage of NEAT1+ MNs; FIG. 4G: percentage of cytoplasmic NEAT1+ MNs; Scale bar: 10 um. * P<0.05, * * P<0.01, * * * P<0.001.

Figure 5A:
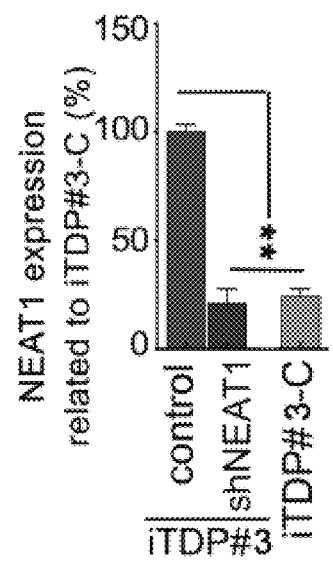
Figure 5B:
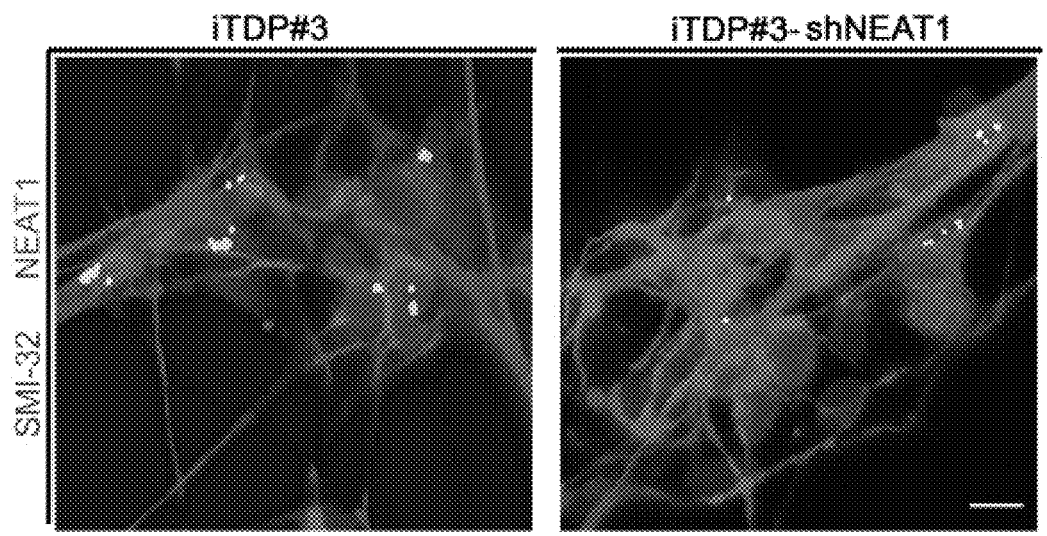
Figure 5C:
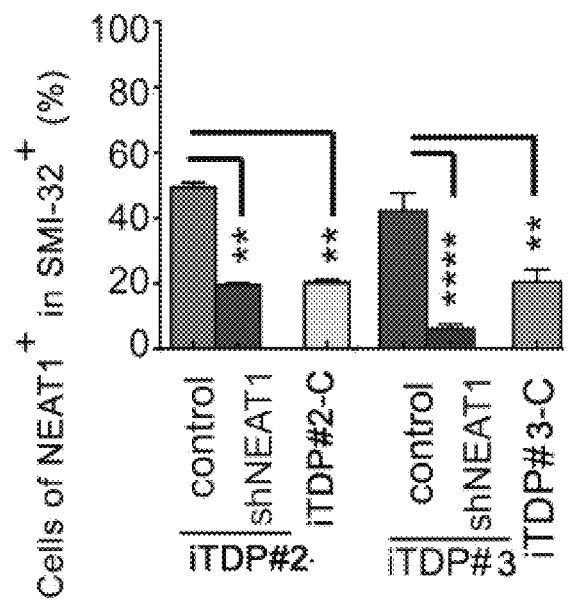
Figure 5D:
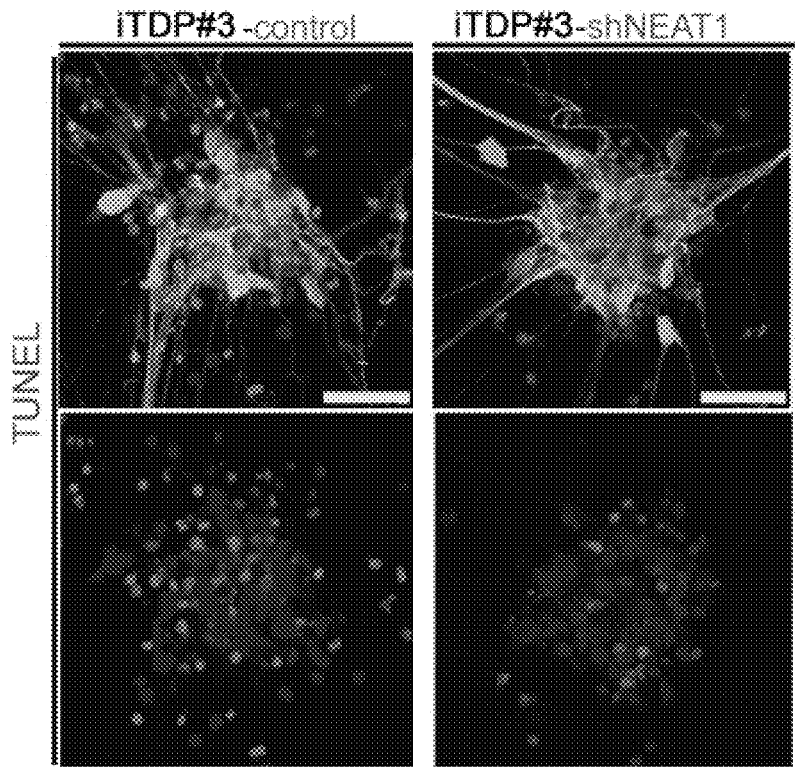
Figure 5E:
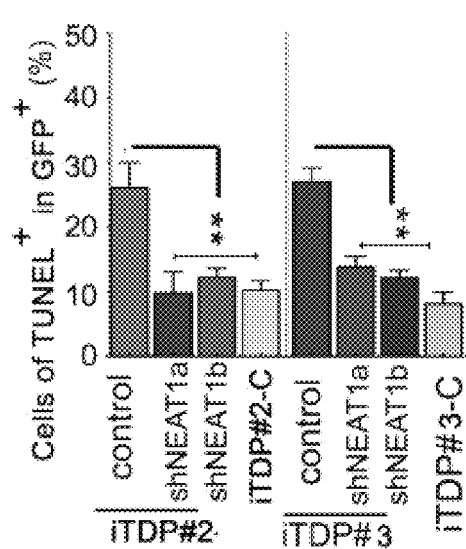
Figure 5F:
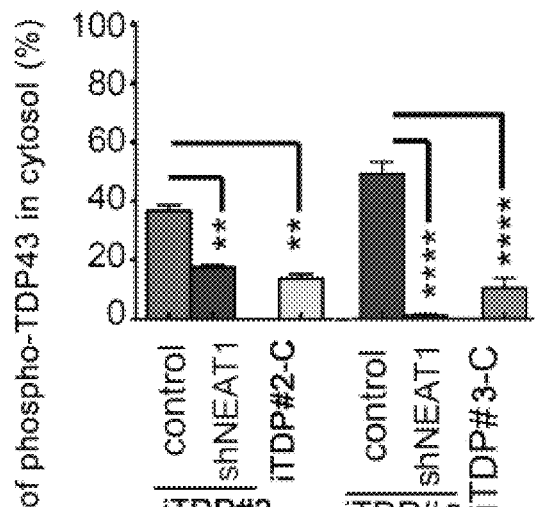
Figure 5G:
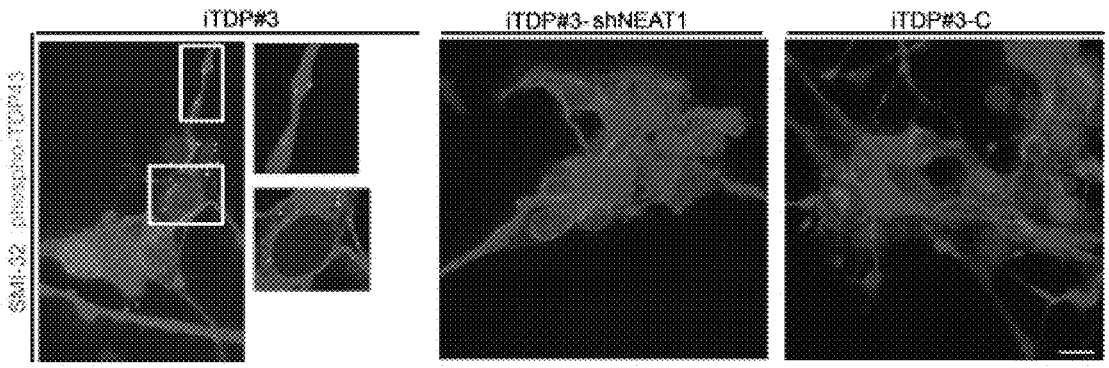
Figure 5H:
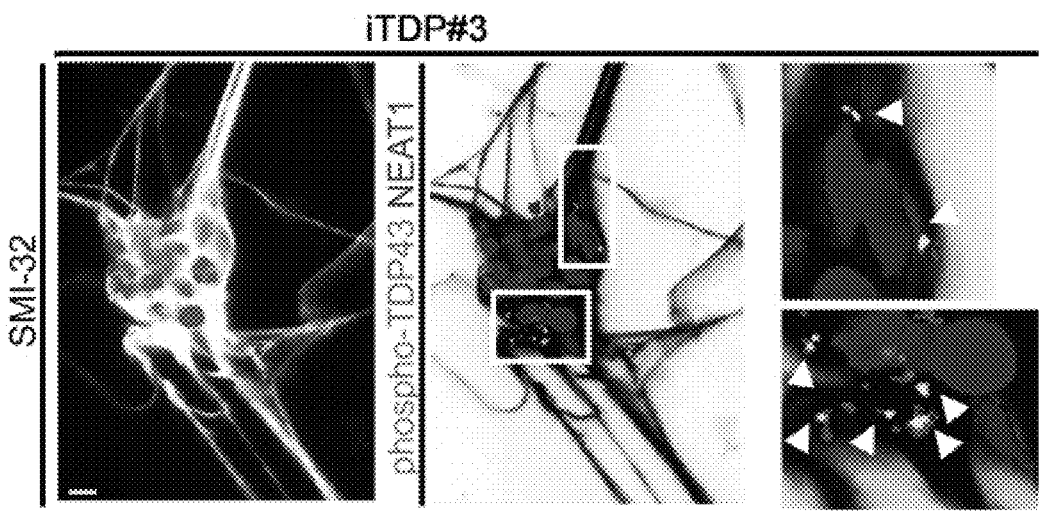
Figure 5I:
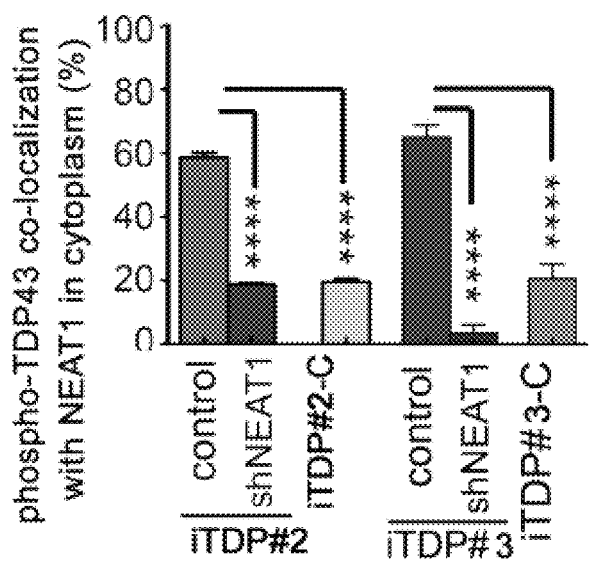

FIGS. 5A to 5I shows that NEAT1 knockdown rescues MN degeneration and TDP43 associated aggregation. FIG. 5A: Validation of NEAT1 knockdown in iTDP #3 derived MN by Q-PCR. FIGS. 5B and 5C: Validation of knockdown NEAT1 in iTDP #2 and iTDP #3 derived MN by in situ hybridization. Scale bar: 10 um. TUNEL assay shows that knockdown NEAT1 rescued degeneration of iTDPs-derived MNs. Scale bar: 50 um; FIG. 5D: representative images of TUNEL assay in NEAT1 knockdown MNs derived from iTDP #3; FIG. 5E: quantification of TUNEL+ in GFP+ neuron derived from iTDP #2 and iTDP #3. FIGS. 5F and 5G: NEAT1 knockdown rescued TDP43 aggregates in iTDP #2 and iTDP #3 derived MNs. Scale bar: 10 um. FIGS. 5H and 5I: NEAT1 colocalized with TDP43+ aggregates in iTDP #2 and iTDP #3 derived MNs. Scale bar: 10 um * P<0.05,  P<0.01, * P<0.001, **** P<0.0001.

Figure 6A:
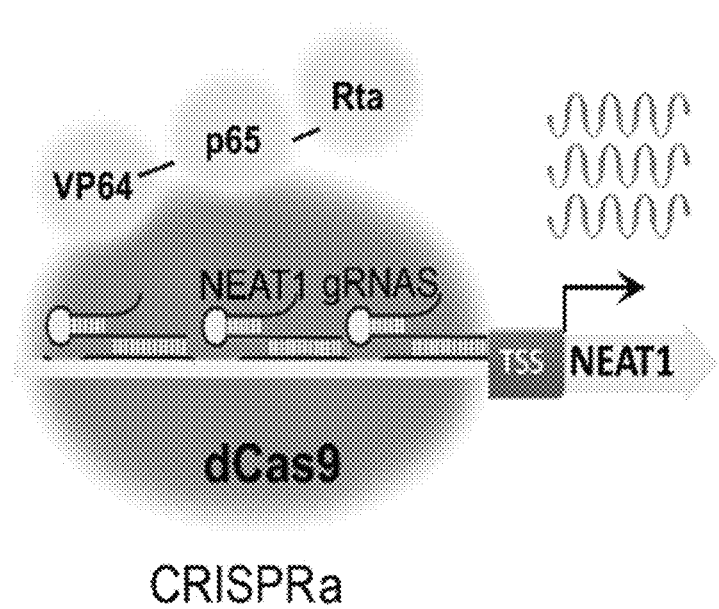
Figure 6B:
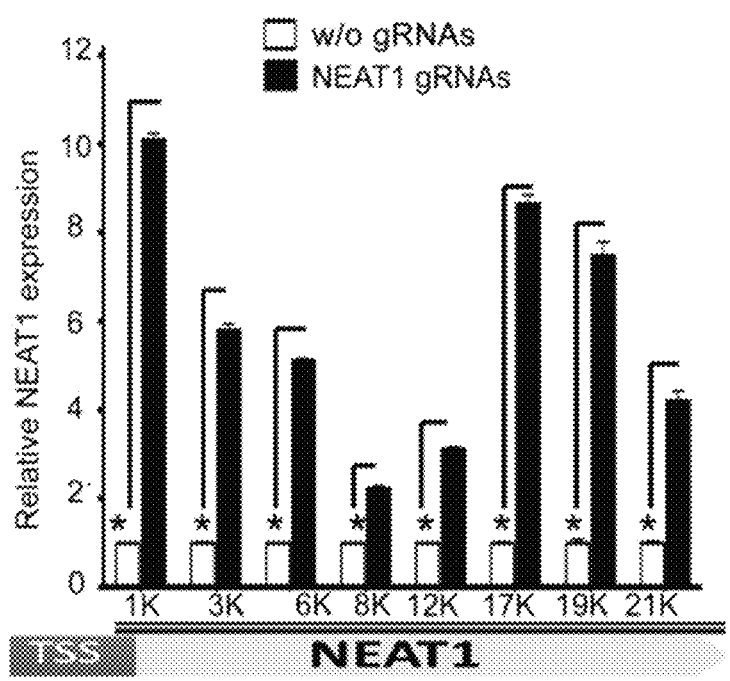
Figure 6C:
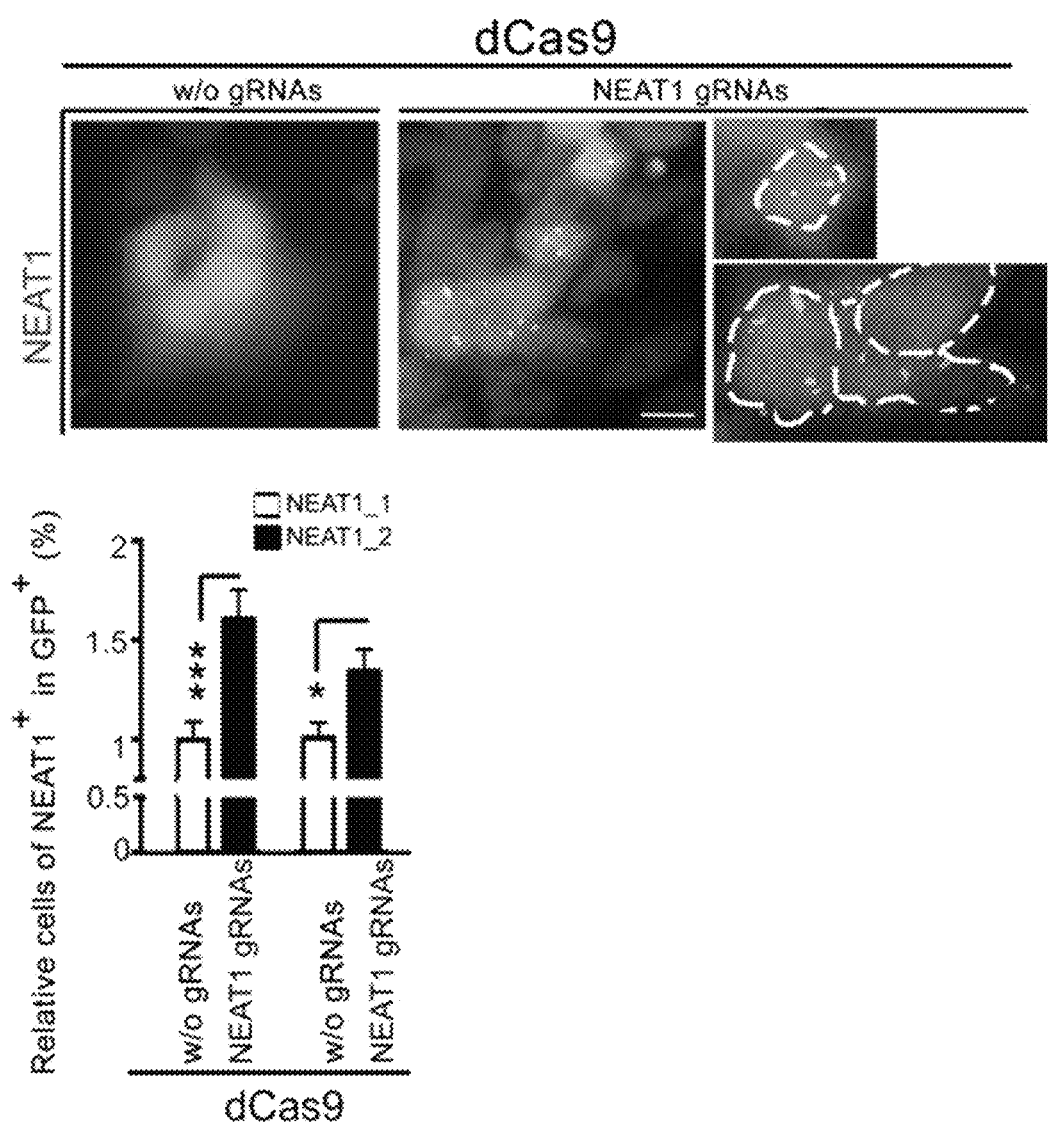
Figure 6D:
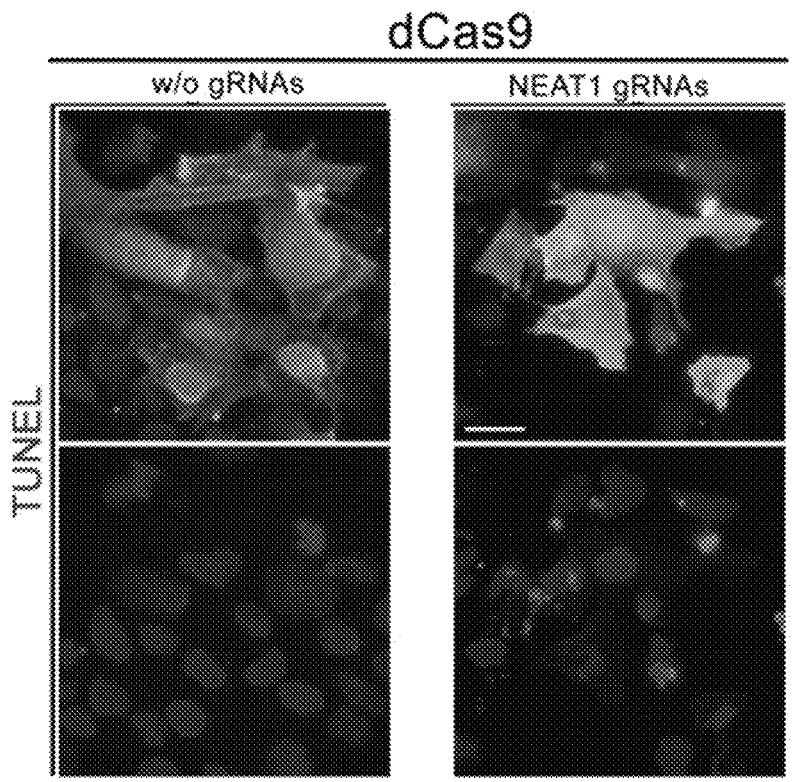
Figure 6E:
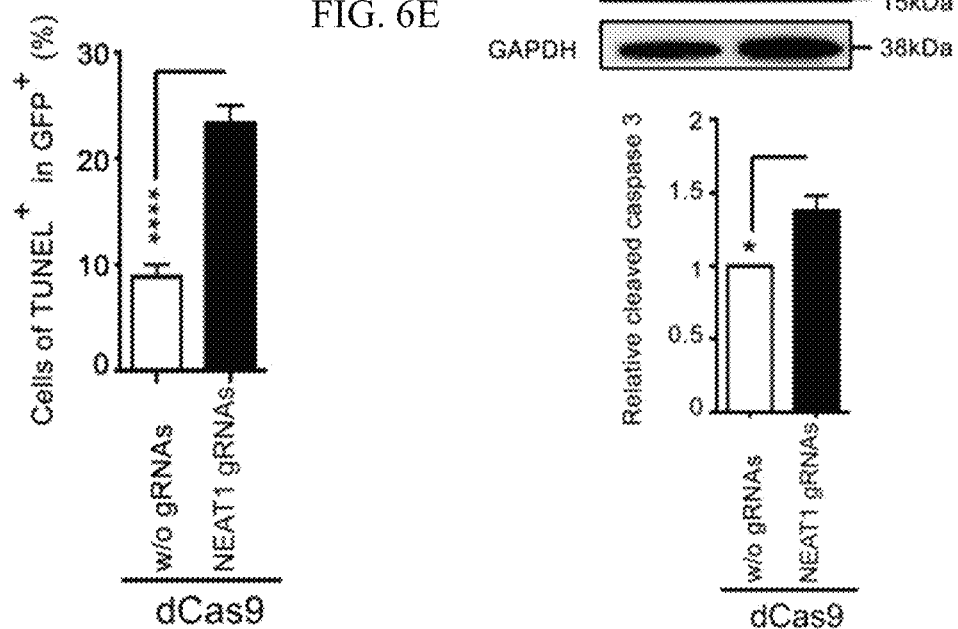
Figure 6F:
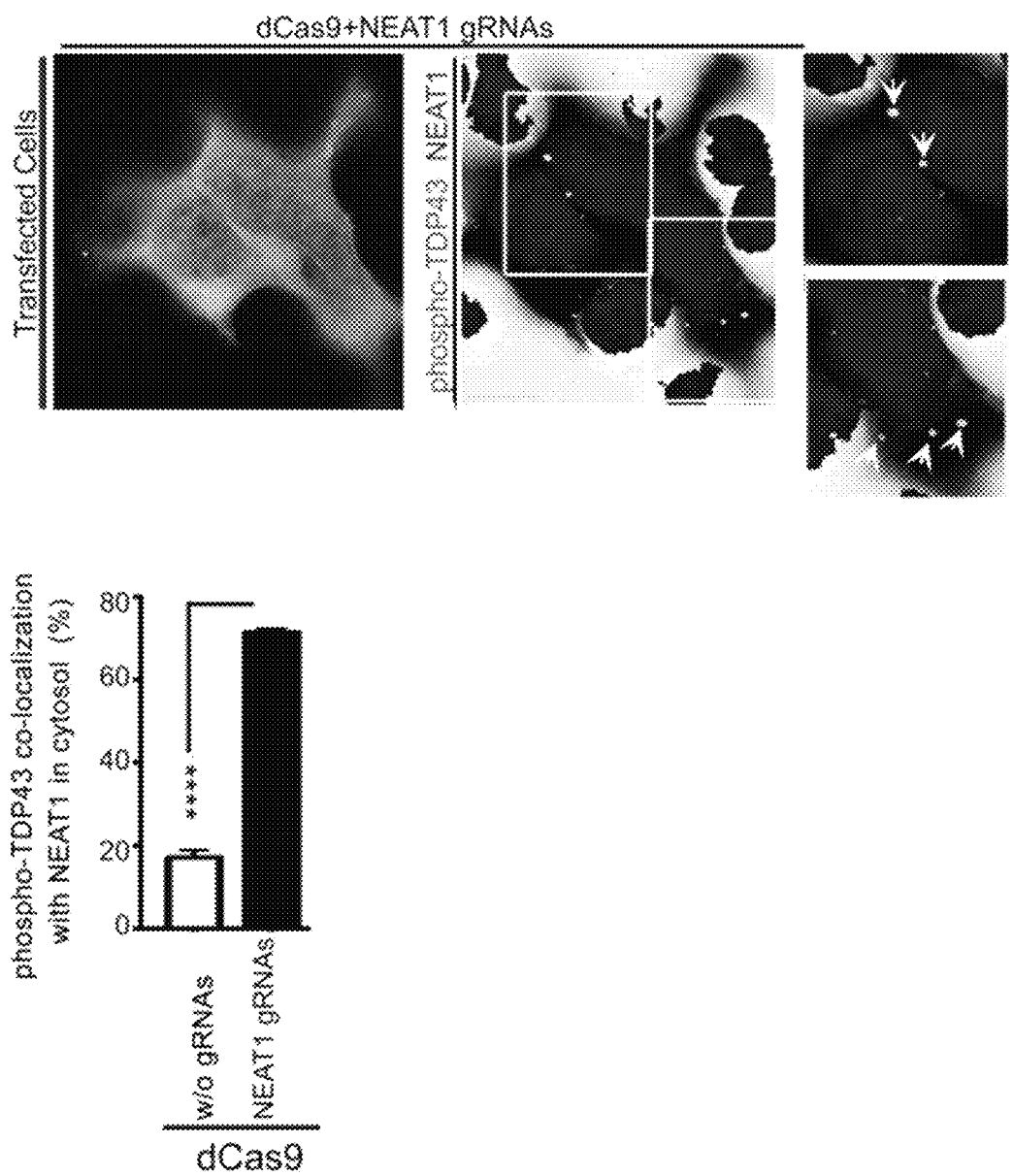

FIGS. 6A to 6F shows that endogenous NEAT1 promotes TDP43 aggregation and MN degeneration. FIG. 6A: Schematic shows CRISPR-a induced endogenous NEAT1 expression in hESCs derived neuron progenitors (NPC). FIG. 6B: Relative NEAT1 expression in NEAT1 gRNAs simultaneously transfected NPCs related to no gRNAs. FIG. 6C: In situ hybridization shows endogenous NEAT1 upregulated by NEAT1 gRNAs on day 5 post-transfection. Scale bar: 10 um. FIG. 6D: TUNEL analysis of neuron death. FIG. 6E: Neural cell death is detected with immunostaining of cleaved Caspase3 fragments in NEAT1 upregulated cell lysates. Scale bar: 10 um. FIG. 6F: FISH and ICC shows increased TDP43 oligomer and NEAT1 co-localization in NEAT1 gRNAs treated NPCs. Scale bar: 10 um. * P<0.05,  P<0.01, * P<0.001, **** P<0.0001.

Figure 7A:
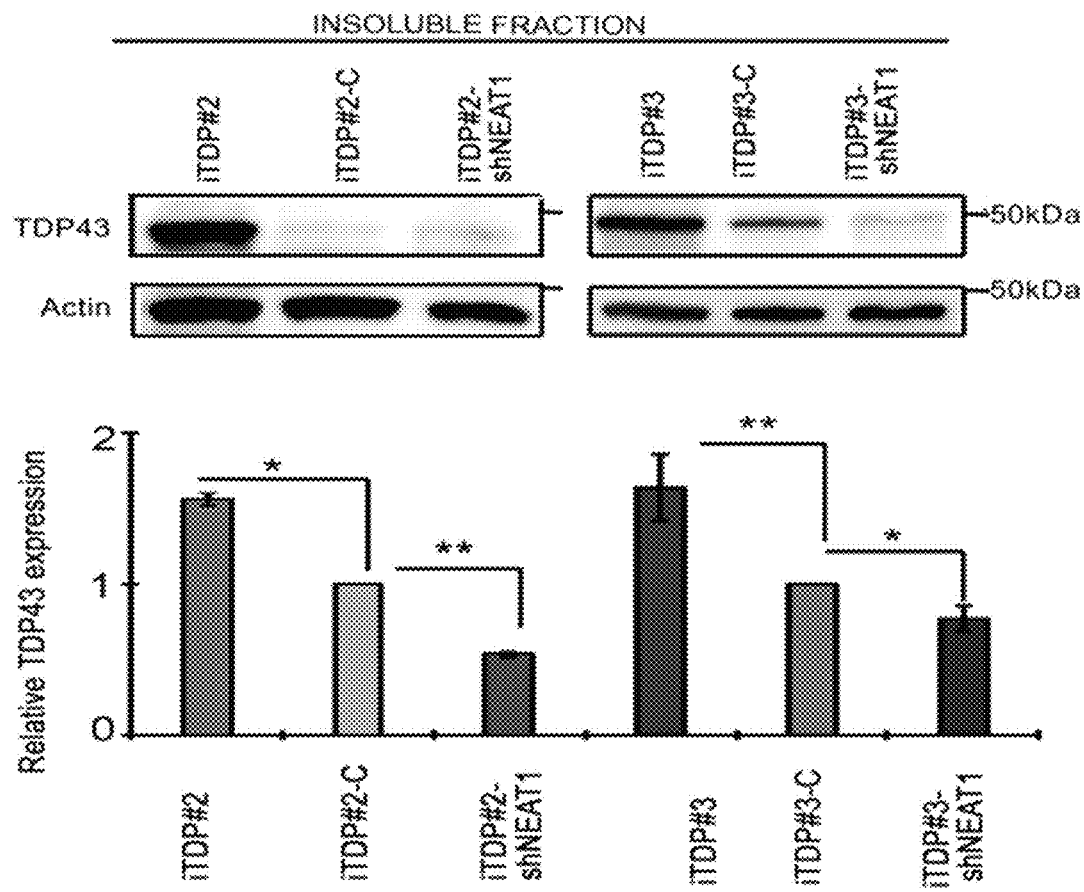
Figure 7B:
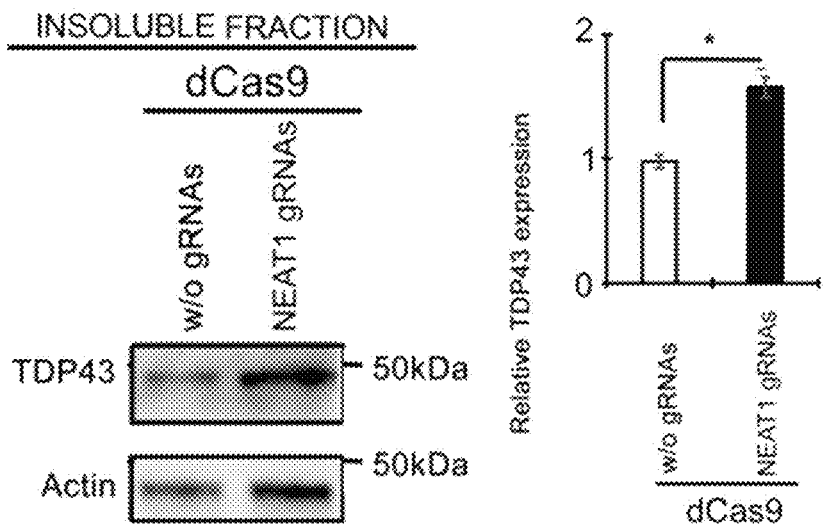

FIGS. 7A to 7B shows that NEAT1 is involved in TDP43 associated inclusions. FIG. 7A: Excessive accumulation of insoluble TDP43 in iTDP #2 and iTDP #3 derived MNs. NEAT1 knockdown reduced insoluble TDP43 accumulation. FIG. 7B: Elevation of insoluble TDP43 in NEAT1 gRNAs targeted NPCs. * P<0.05,  P<0.01, * P<0.001, **** P<0.0001.

Figure 8A:
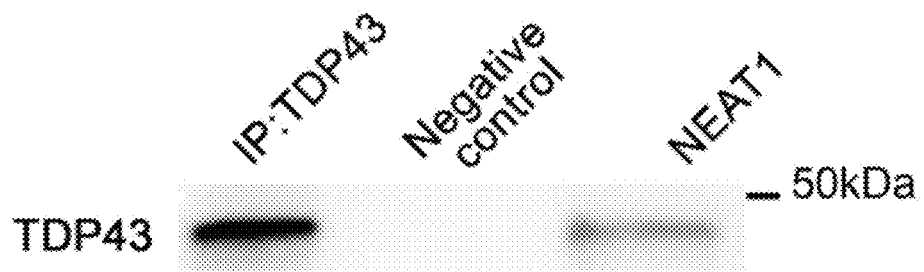
Figure 8B:
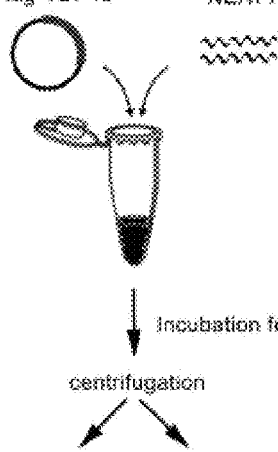
Figure 8B:
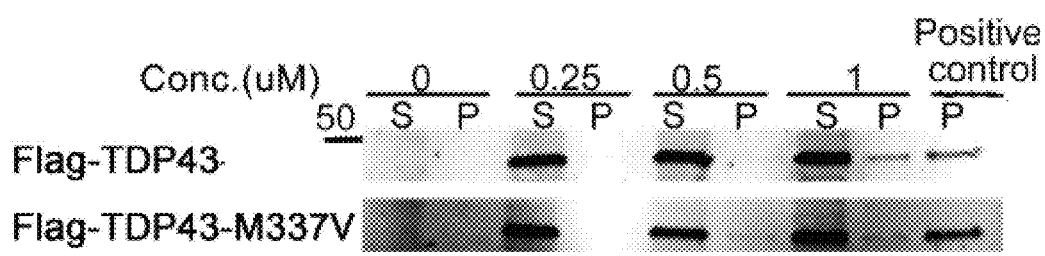
Figure 8C:
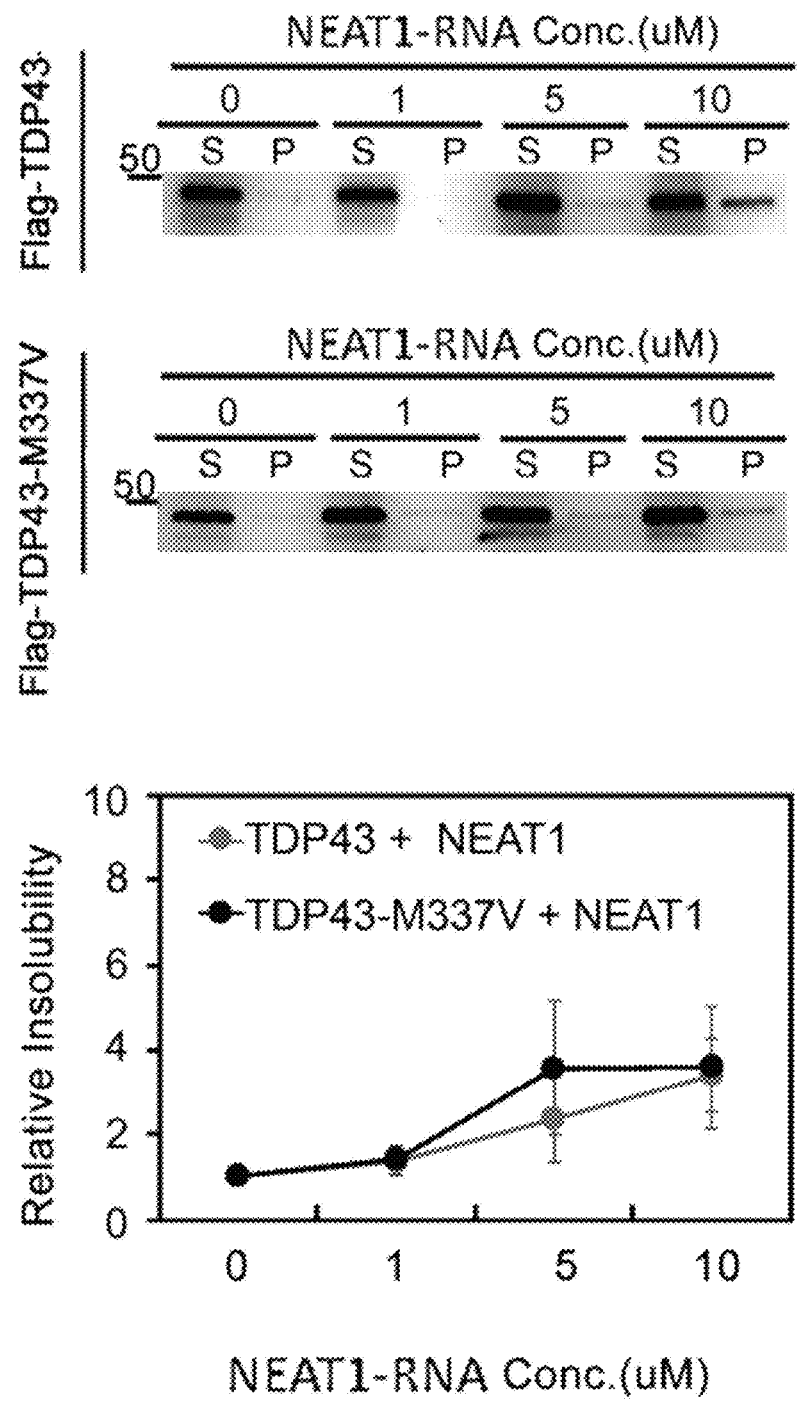
Figure 8D:
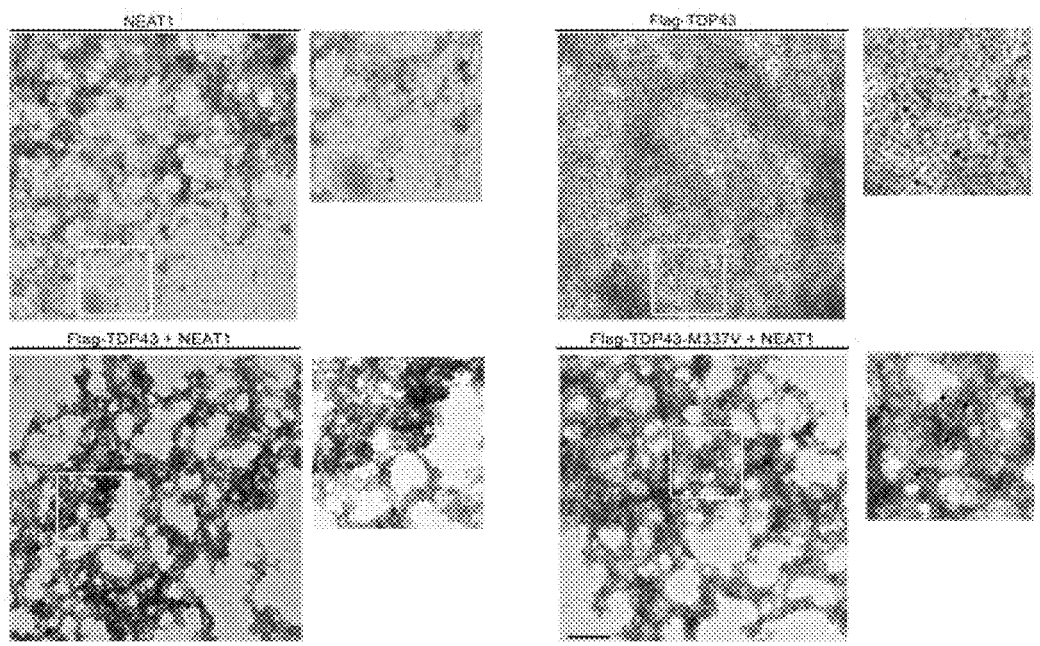

FIGS. 8A to 8D shows that NEAT1 promotes insolubility by direct interaction with TDP43 and TDP43-M337V. FIG. 8A: NEAT1 pulldown assay indicates interaction with TDP43. FIG. 8B: schematic shows cell-free system for investigating concentration-dependent insolubility of TDP43 and TDP43-M337V. FIG. 8C: NEAT1 promotes insolubility by direct interaction with TDP43 or TDP43-M337V. FIG. 8D: Morphologies of insoluble TDP43 and TDP-M337V promoted by NEAT1 visualized by immunogold TEM staining. The arrows indicate immunogold-labeled TDP43 or TDP43-M337V. Scale bar is 200 nm. * P<0.05,  P<0.01, * P<0.001, **** P<0.0001.

Figure 9A:
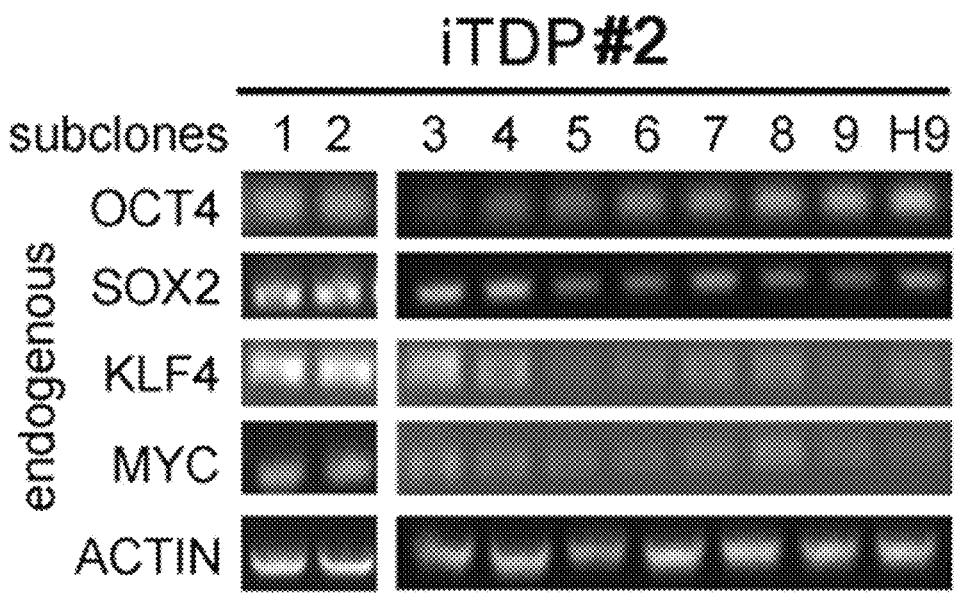
Figure 9B:
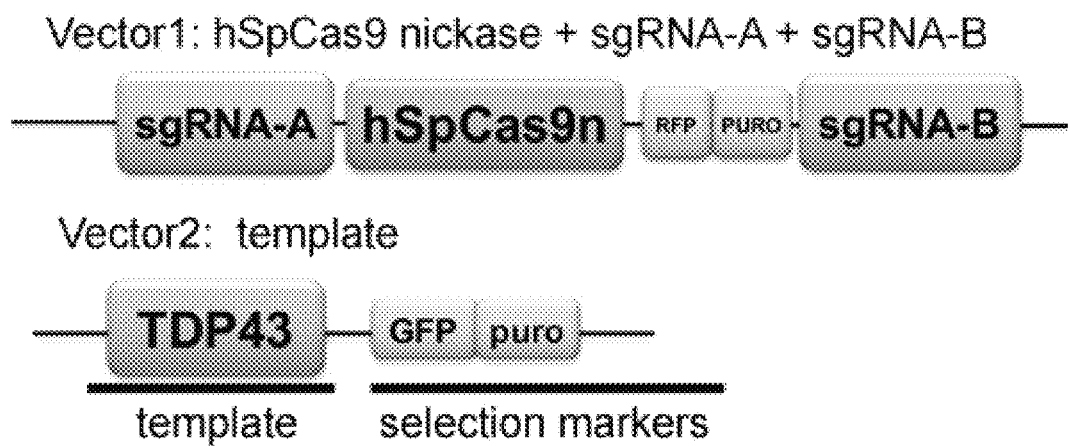
Figure 9C:
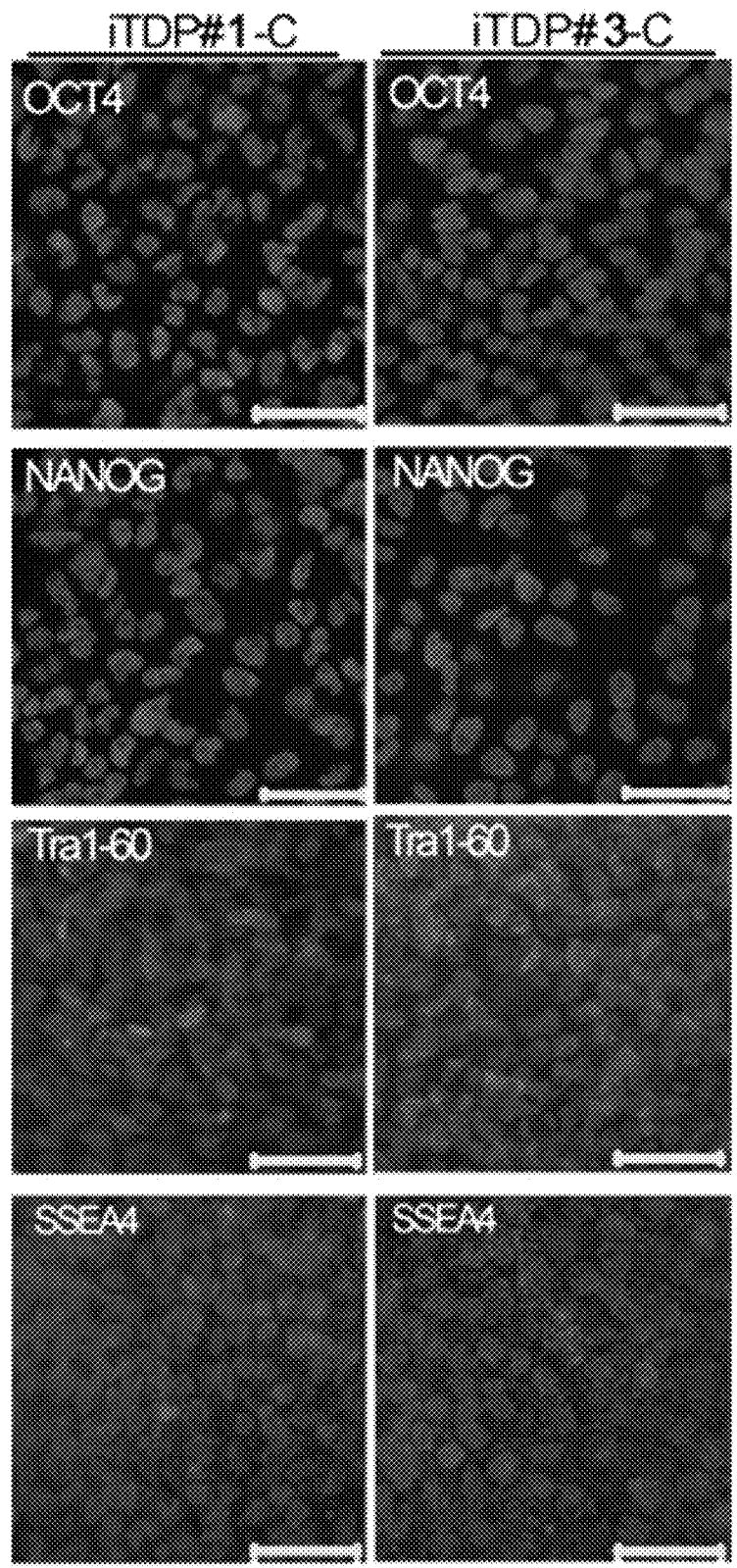

FIGS. 9A to 9C: shows characterization of pluripotent gene expression in iPSCs by RT-PCR and iTDP #1-C and iTDP #3-C by immunostaining pluripotent markers: OCT4, NANOG, TRA1-60 and SSEA4.

Figure 10:
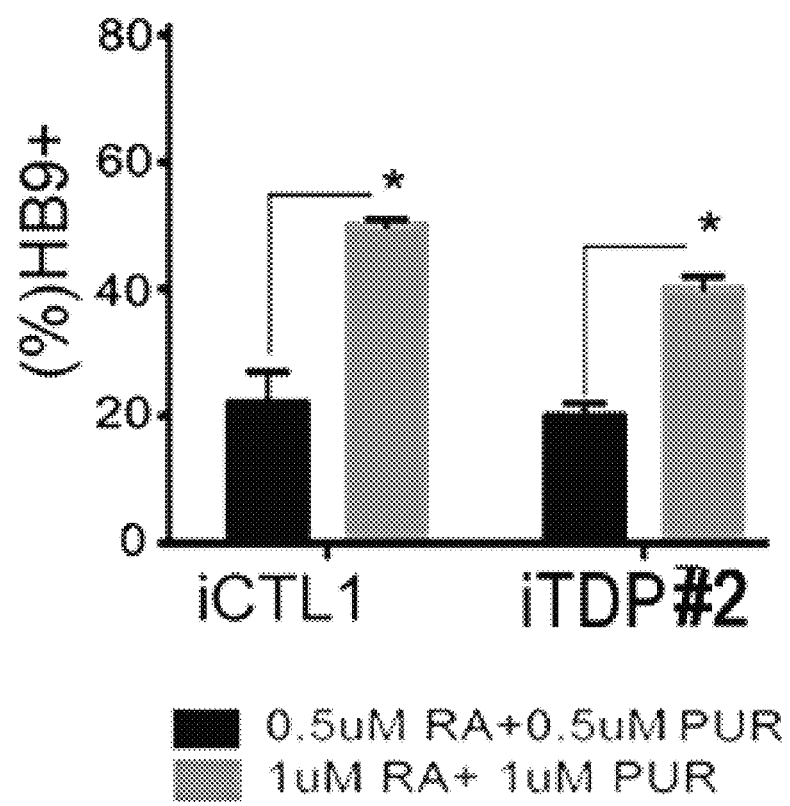

FIG. 10 shows optimizing RA and PUR concentration for generation of HB9+MN population derived from iCTL1 and iTDP #2.

Figure 11A:
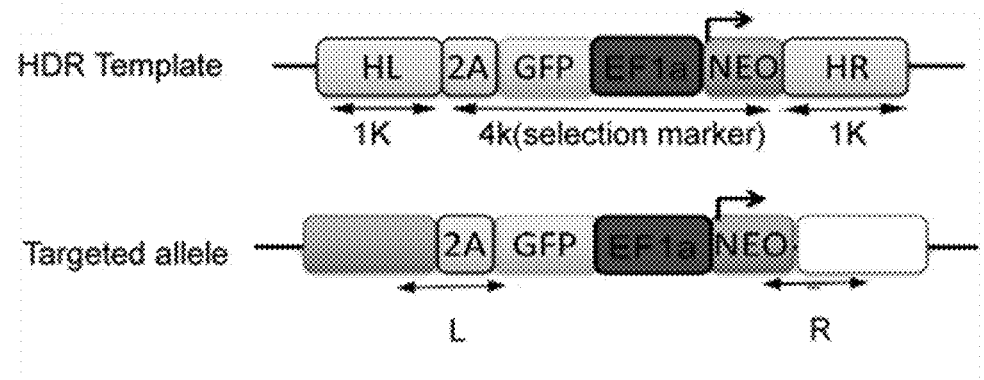
Figure 11B:
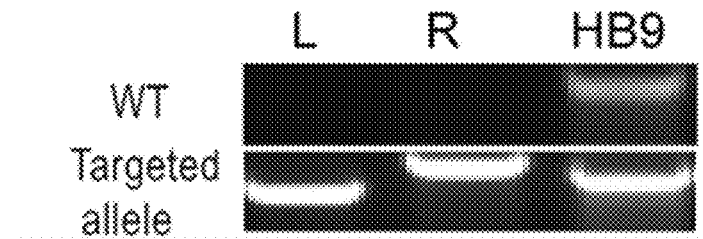
Figure 11C:
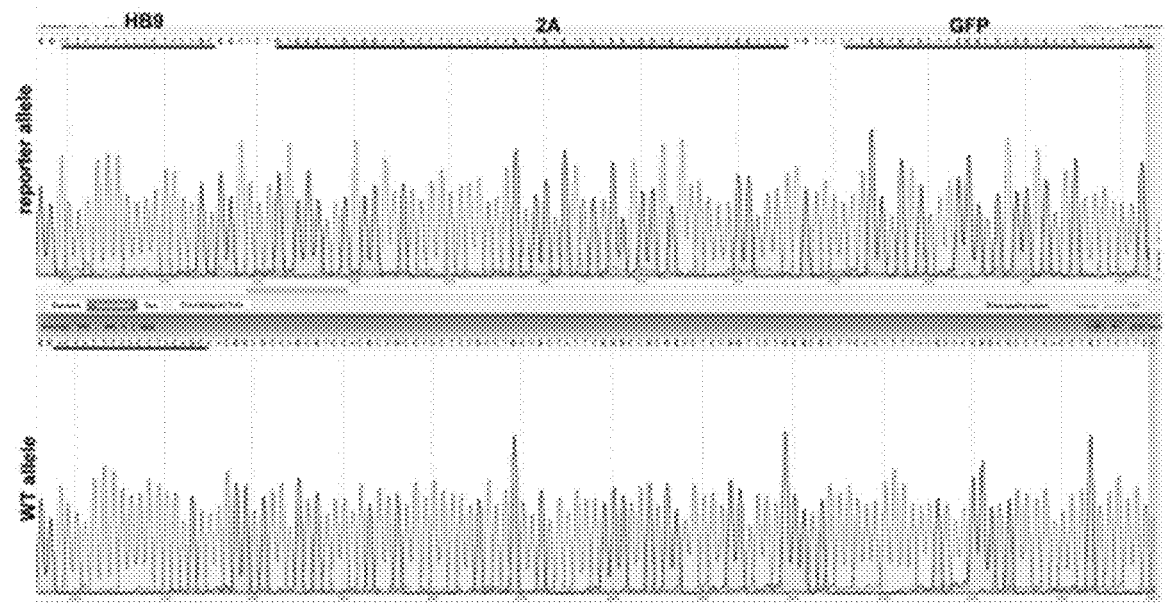

FIGS. 11A to 11C: shows that characterization of CRISPR-Cas9n generates HB9::GFP iPSC lines.

Figure 12A:
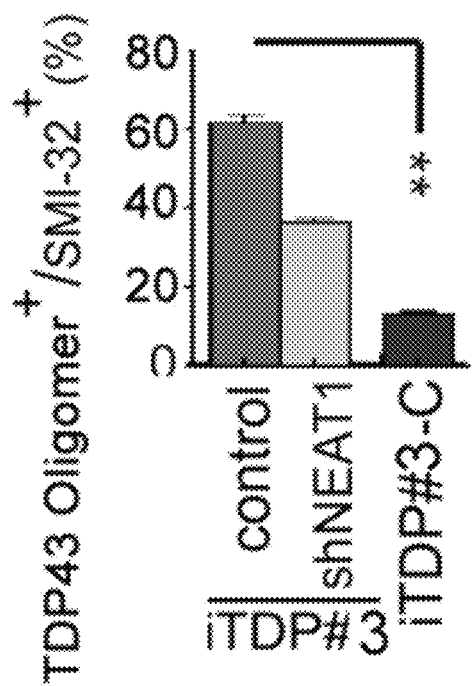
Figure 12B:
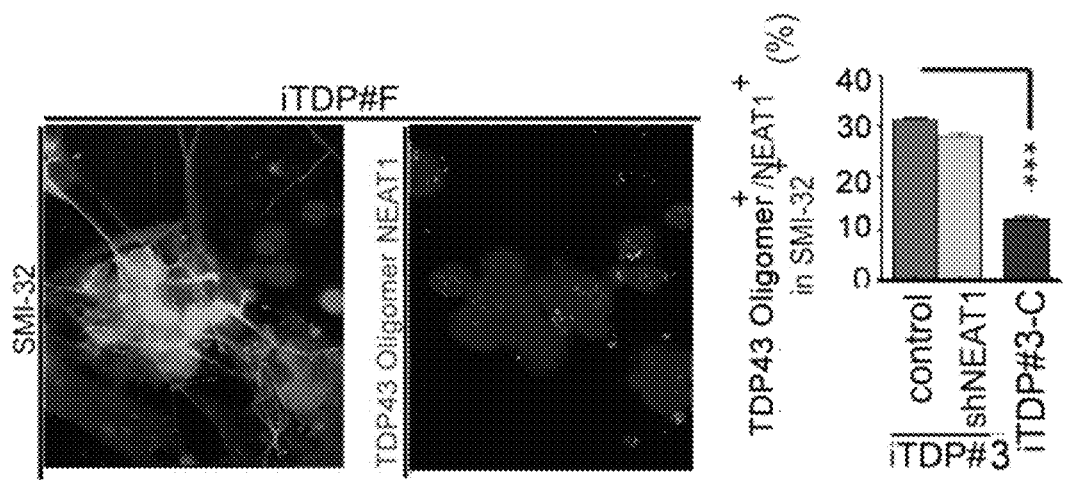

FIGS. 12A to 12B shows that NEAT1 Knockdown does not rescue TDP43 oligomerization. FIG. 12A: NEAT1 Knockdown rescued TDP43 aggregates in iTDP #3 derived MNs. FIG. 12B: A few percentage of NEAT1 colocalized with TDP43+ oligomer in iTDP #3 derived MNs. * P<0.05,  P<0.01, * P<0.001, **** P<0.0001.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "gene" refers to a polynucleotide containing at least one open reading frame (ORF) that is capable of encoding a particular polypeptide or protein after being transcribed and translated.

As used herein, the term "knockdown" refers to the expression of a gene is reduced. The reduction can occur either through genetic modification or by treatment with a reagent such as a short DNA or RNA oligonucleotide that has a sequence complementary to either gene or an mRNA transcript.

As used herein, the term "short nucleic acid molecule" refers to any nucleic acid molecule capable of modulating gene expression. The terms "short interfering nucleic acid", "siNA" or "siNA molecules," "short interfering nucleic acid molecule," or "short interfering oligonucleotide molecule" refer to any nucleic acid molecule capable of inhibiting, downregulating or knocking down gene expression. Typically, short interfering nucleic acid molecules are composed primarily of RNA, and may be referred to as "short interfering RNA" or "siRNA." A siNA may, however, include nucleotides other than RNA, such as in DNAi (interfering DNA), or other modified bases. Thus, the term "RNA" as used herein means a molecule comprising at least one ribonucleotide residue and includes double stranded RNA, single stranded RNA, isolated RNA, partially purified, pure or synthetic RNA, recombinantly produced RNA, as well as altered RNA such as analogs or analogs of naturally occurring RNA.

As used herein, the term "hybridizing" refers to any process by which a strand of nucleic acid binds with a complementary strand through base pairing.

As used herein, the term "at risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

As used herein, the term "prevent the onset of" means to prevent the development a condition or disease in a subject who is at risk for developing the disease or condition. In certain embodiments, a subject at risk for developing the disease or condition receives treatment similar to the treatment received by a subject who already has the disease or condition.

As used herein, the term "delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

As used herein, the terms "treat," "treating" or "treatment," and other grammatical equivalents include alleviating, inhibiting or reducing symptoms, reducing or inhibiting severity of, reducing incidence of, prophylactic treatment of, reducing or inhibiting recurrence of, preventing, delaying onset of, delaying recurrence of, abating or ameliorating a disease or condition symptoms, ameliorating the underlying metabolic causes of symptoms, inhibiting the disease or condition. The terms further include achieving a therapeutic benefit. Therapeutic benefit is meant to refer to eradication or amelioration of the underlying disorder being treated, and/or the eradication or amelioration of one or more of the physiological symptoms associated with the underlying disorder such that an improvement is observed in the patient.

As used herein, the terms "prevent," "preventing" or "prevention," and other grammatical equivalents, include preventing additional symptoms, preventing the underlying metabolic causes of symptoms, inhibiting the disease or condition, e.g., arresting the development of the disease or condition and are intended to include prophylaxis. The terms further include achieving a prophylactic benefit. For prophylactic benefit, the compositions are optionally administered to a patient at a risk of developing a particular disease, to a patient reporting one or more of the physiological symptoms of a disease, or to a patient at risk of reoccurrence of the disease.

As used herein, the terms "effective amount" or "therapeutically effective amount" refer to a sufficient amount of at least one agent being administered which achieve a desired result, e.g., to relieve to some extent one or more symptoms of a disease or condition being treated. In certain instances, the result is a reduction and/or alleviation of the signs, symptoms, or causes of a disease, or any other desired alteration of a biological system.

As used herein, "subject" refers to either a human or non-human animal.

As used herein the term "candidate agent" refers to any organic or inorganic molecule, including modified and unmodified nucleic acids such as antisense nucleic acids, RNA interference agents such as siRNA or shRNA, peptides, peptidomimetics, receptors, ligands, drugs, prodrugs, metabolite analogs, and antibodies. In one aspect, the present invention provides a method of reducing neurodegeneration and/or TDP43 associated aggregation, comprising knocking down the expression of NEAT1 or LncRNA NEAT1.

Coupling iPSCs and CRISPR provides a useful platform to unravel the complex disease causing mechanisms of ALS for developing potential therapeutic strategies. The present invention combines reprograming, iPSC differentiation approaches and genome engineering to explore the roles of lncRNAs regulated by TDP43-M337V missense mutation in human ALS motor neurons. The present disclosure has recapitulated ALS phenotypes, including progression of TDP43 pathology, MN death and mitochondrial dysfunctions. The present invention also defines the novel mechanisms of Nuclear Paraspeckle Assembly Transcript 1 (NEAT1) in TDP43 proteinopathy that contributed to motor neuron dysfunction and subjected to degeneration. Notably, the present disclosure finds TDP43 missense mutation dedicated to NEAT1 transcription and following dislocation in cytoplasm for the further associated with TDP43 aggregation. In cell and cell-free system, the cytoplasmic NEAT1 acts as a scaffold for direct interaction with TDP43 and causes further aggregation. Finally, the present invention reveals the role of NEAT1 in TDP43 proteinopathy of ALS and suggests the potential prevention of TDP43 aggregation for therapeutic targeting in ALS.

The present disclosure defines novel role of NEAT1 as a scaffold for promoting TDP43/TDP43-M337V insolubility and aggregation. Manipulation of NEAT1 provides evidence of NEAT1 promoted neural death in a manner of TDP43 aggregation dependence. While NEAT1 is correlated with TDP43 aggregation, this paraspeckle essential RNA may also provide another role in TDP43-M337V mutant ALS due to the unusual presence of cytoplasmic NEAT1 in ALS MNs. TDP43-M337V missense mutation is the cause of cytoplasmic TDP43 aggregation in patient iPSC derived MNs, and NEAT1 is involved as scaffold for protein recruitment.

The present disclosure has shown that lncRNA NEAT1 plays a vital role involving cytoplasmic TDP43 aggregation/inclusions. As a scaffold, NEAT1 traps TDP43/TDP43-M337V to increase insolubility and further induces pathological aggregation. Reducing the excessive amount of NEAT1 could not only rescue cytoplasmic TDP43 aggregation, but also rescue motor neuron degeneration. Enhancing endogenous NEAT1 expression in normal neuron cells, the cell death was recapitulated and validated by two cell readouts. As a result, NEAT1 could play a therapeutic target for treating a neurodegenerative disorder such as motor neuron degeneration of ALS. Accordingly, in one aspect, the present disclosure provides a method of reducing neurodegeneration and/or TDP43 associated aggregation, comprising knocking down the expression of Nuclear Paraspeckle Assembly Transcript 1 (NEAT1) or LncRNA NEAT1.

In another aspect, the present invention provides a method of selecting a gene of interest associated with neurodegeneration and/or TDP43 associated aggregation, comprising providing iPSCs from a subject having TDP43-M337V mutation, differentiating the iPSCs to motor neuron cells, knocking out the gene of interest in the motor neuron cells, and determining the TDP43 associated aggregation in the motor neuron cells, wherein the elevated level of TDP43 associated aggregation indicates the likelihood that the gene of interest is involved in neurodegeneration.

According to the present invention, coupling iPSCs and CRISPR provides a useful platform to unravel the complex disease causing mechanisms of ALS for developing potential therapeutic strategies. The present invention combines reprograming, iPSC differentiation approaches and genome engineering to explore the roles of a gene regulated by TDP43-M337V missense mutation in human ALS motor neurons. Accordingly, a gene of interest associated with neurodegeneration and/or TDP43 associated aggregation can be selected by the method of the present invention. The iPSCs are obtained from a subject having TDP43-M337V mutation. A gene of interest in the iPSC is knocked out. The iPSCs are differentiated to motor neuron cells and then and the TDP43 associated aggregation is measured to determine whether the gene of interest is involves in neurodegeneration.

In some embodiments, a gene of interest can be knocked out by clustered regularly interspaced short palindromic repeats (CRISPR) and CRISPR associated proteins (Cas) system, in which at least two vectors are used to respectively transport a Cas enzyme and RNAs that hybridize with the target sequences in genomic loci of the nucleic acid, into the cell. The Cas enzyme is subsequently recruited by the RNAs that hybridize with the target sequences in genomic loci to cleave the expressed modified gene product. In some embodiments, the Gas enzyme is a type II CRISPR system enzyme. In some embodiments the type II CRISPR system enzyme is a Cas9 enzyme. In some embodiments, the Cas9 enzyme is *S. pneumoniae, S. pyogenes*, or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell.

In another aspect, the present invention provides a method for screening a candidate agent that reduces neurodegeneration and/or TDP43 associated aggregation in a cell, the method comprising: (a) contacting a cell with a candidate drug, and (b) assessing expression level of NEAT1 or LncRNA NEAT1 in the cell, wherein if the expression level of NEAT1 or LncRNA NEAT1 in the cell is lower than that in an untreated cell, then the candidate agent reduces neurodegeneration and/or TDP43 associated aggregation. In one embodiment, the candidate agent has potential to treat or prevent a neurodegenerative disorder, delay or prevent the onset of a neurodegenerative disorder or reduce a risk for developing a neurodegenerative disorder.

A variety of different pharmaceutical/therapeutic agents can be used in conjunction with the methods described herein and include, but are not limited to, small molecules, proteins, antibodies, peptides and nucleic acids. In general, agents useful in the methods described herein will down-regulate NEAT1 or LncRNA NEAT1.

In another aspect, the present invention provides a method of treating or preventing a neurodegenerative disorder, delaying or preventing the onset of a neurodegenerative disorder or reducing a risk for developing a neurodegenerative disorder in a subject, comprising administering to the subject an agent that knocks down, downregulates or inhibit NEAT1 expression; or an agent inhibiting, silencing or downregulating LncRNA NEAT1.

In a further aspect, the present invention provides a method for determining whether a subject is suffering from, or at a risk of developing a neurodegenerative disorder, comprising measuring the presence of cytoplasmic NEAT1 in a biological sample, wherein the presence is an indicative of the risk of developing a neurodegenerative disorder.

In one embodiment, the agent is a short nucleic acid molecule. Examples of the short nucleic acid molecule include, but are not limited to, short interfering RNA (siRNA), double stranded RNA (dsRNA), micro RNA (miRNA), short hairpin RNA (shRNA), and interfering DNA (DNAi) molecules. In a certain embodiment, the short nucleic acid molecule is a siRNA. The present siNA may be used with or without additional factors. The siNA molecules can also be chemically modified by introduction of a 2'-O-Methoxy modification and thus made nuclease resistant. In some embodiments, the short nucleic acid molecule has the nucleotide sequence of SEQ ID NO:1 or 2.

```
                                              (SEQ ID NO: 1)
CCGGGTGAGAAGTTGCTTAGAAACTTTCCCTCGAGGGAAAGTTTCTAAGC
AACTTCTCAC TTTTT (SEQ ID NO: 2)
CCGGCTGGTATGTTGCTCTGTATGGTAAGCTCGAGCTTACCATACAGAGC
AACATACCAGTTTTT (SEQ ID NO: 34)
GTGAGAAGTTGCTTAGAAACTTTCC (SEQ ID NO: 35)
CTGGTATGTTGCTCTGTATGGTAAG
```

Accordingly, the present disclosure provides a short nucleic acid molecule, comprising a nucleotide sequence consisting of SEQ ID NO:1, 2, 33 or 34 or a derivative thereof. The short nucleic acid molecule can knockdown NEAT1 or LncRNA NEAT1, whereby treating or preventing a neurodegenerative disorder, delaying or preventing the onset of a neurodegenerative disorder or reducing at a risk for developing a neurodegenerative disorder in a subject.

In some embodiments, the neurodegenerative state can include, but is not limited to, Parkinson's disease and the parkinsonisms including progressive supranuclear palsy, Alzheimer's disease, motor neuron disease (such as amyotrophic lateral sclerosis (ALS) and spinal muscular atrophies (SMA)), Lewy body dementia, essential tremor, multiple sclerosis, dyskinesia, dystonia, ataxia, Huntington's disease, multiple system atrophy, myoclonus, progressive supranuclear palsy, Rhett syndrome, spasticity, Tourette syndrome, Bell's palsy, herpes ophthalmicus, herpes oticus, neurodegeneration due to chronic graft-versus-host-disease, and neurodegeneration due to viral and iatrogenic causes, and any other neurodegenerative disease mediated by upregulation or NEAT1 or LncRNA NEAT1.

A motor neuron disease (MND) is any of several neurodegenerative disorders that selectively affect motor neurons, the cells that control voluntary muscles of the body. In some embodiments, the motor neuron degeneration disease described in the present disclosures includes amyotrophic lateral sclerosis (ALS) and spinal muscular atrophies (SMA). In some embodiments, the ALS is familia ALS or sporadic ALS.

The agent of the invention may be employed, in another embodiment, in combination with a non-sterile or sterile carrier or carriers for administration to cells, tissues or organisms, such as a pharmaceutical carrier suitable for administration to a subject. Such compositions comprise, for instance, a media additive or a therapeutically effective amount of a recombinant virus of the invention and a pharmaceutically acceptable carrier or excipient. Such carriers may include, but are not limited to, saline, buffered saline, dextrose, water, glycerol, and combinations thereof. The formulation should suit the mode of administration.

The agents of the invention may be employed alone or in conjunction with other compounds, such as additional therapeutic compounds.

The pharmaceutical compositions may be administered in any effective, convenient manner including, for instance, administration by intravascular (i.v.), intramuscular (i.m.), intranasal (i.n.), subcutaneous (s.c.), oral, rectal, or intravaginal delivery routes, or by any means in which the recombinant virus/composition can be delivered to tissue (e.g., needle or catheter). Alternatively, topical administration may be desired for insertion into neural cells.

Without further elaboration, it is believed that one skilled in the art can, based on the disclosure herein, utilize the present disclosure to its fullest extent. The following specific examples are, therefore, to be construed as merely descriptive, and not limiting of the remainder of the disclosure in any way whatsoever.

EXAMPLES

Materials and Methods
Cell Culture:

Mouse embryonic fibroblasts (MEFs) and 293T cells were cultured in DMEM supplemented with 10% fetal bovine serum (FBS), 1× non-essential amino acid (NEAA, Invitrogen), 2 mM L-glutamine (Invitrogen) and 1× penicillin/streptomycin (Invitrogen). Human iPSCs were cultured on MEF feeders ($2\times10^4$ cells/cm$^2$) in DMEM/F12 medium plus 20% Knockout Serum Replacement (Invitrogen, Carlsbad, Calif.) and 4~10 ng/ml bFGF (Sigma-Aldrich). Human somatic cells were cultured in a medium similar to the MEF medium described above. For both MEFs and HFs, low passage-number (less than 5) cells were used for iPSC reprogramming.

Patient-Specific iPSC Derivation and Characterization:

For this study, we used three ALS patients' dermal fibroblasts through skin biopsy, one male and two females. Three of them were diagnosed as fALS with TDP43-M337V mutation. Patients' iPSC derivation was carried out by overexpression of human OCT4, SOX2, KLF4 and MYC described previously. ESC-like colonies were isolated and characterized by detecting endogenous counterparts of OCT4, SOX2, KLF4 and MYC and immunostaining with pluripotent markers including OCT4, NANOG, Tra1-60 and SSEA4. The iPSCs derived from individual were named iTDP #1, iTDP #2 and iTDP #3. The following Table 1 shows details of patient profile.

TABLE 1 profile of ALS patients and control cases in this study
Demographics of ALS Samples and Control Cases

| Patient | Age of biopsy | Gender | Reprogramming factors[a] | Diagnosis | Mutation |
|---|---|---|---|---|---|
| iTDP#C | 53 | Male | OSKM | Familial ALS | TDP43M337V (A1006 > G)[b] |
| iTDP#D | 60 | Female | OSKM | Familial ALS | TDP43M337V (A1006 > G) |
| iTDP#F | 49 | Female | OSKM | Familial ALS | TDP43M337V (A1006 > G) |
| iCTL1 | 36 | Female | OSKM | Normal control | TDP43M337M |

[a]OSKM: transcription factors of OCT4 (O), SOX2 (S), KLF4 (K), and C-MYC (M).
[b]TDP43: TAR DNA binding protein (TARDBP)

Mn Differentiation:

iPSCs were dissociated with dispase (1 mg/ml) and plated on MEFs plated dishes with hESC medium the day before induction. Motor neuron basal medium (MNBM) contained 0.5×DMEM/F12, 0.5× neurobasal medium, 0.5×N2 supplement, 0.5×B27 supplement, 1×NEAA and 1×glutaMax. In the first 6 days, cells were treated with MNBM supply with SB431542 (2 μM), DMH1 (2 μM), and CHIR99021 (3 μM). Cells were passaged and transferred to a matrigel coated dish with additional supply with Retinoic acid (1 μM) and purmorphamine (PUR) (1 μM) for another 6 days. Neural rosettes were cultured in suspension, and treated with MNSM supply with Retinoic acid (1 μM) and PUR (1 μM) for another 6 days. From day 18, motor neurons maturation were treated with Compound E (0.1 μM), RA (0.1 μM), PUR (0.5 μM), ascorbic acid (400 ng/ml), cAMP (1 μM), and 10 ng/ml of neurotrophic factors including CNTF, BDNF, GDNF and IGF.

Targeting of iPSCs Using Double Nicking CRISPR/Cas9-Mediated Homologous Recombination for HB9 Reporter and Genetic Correction:

The paired guide RNAs were designed based on CRISPR Design Tool among target regions. For TDP43M337V (chr1.11082443) correction, the sequences of paired guide RNAs at chromosome 1 were as follows: 5'-AACTGCTCTGTAGTGCTGCC-3' (SEQ ID NO:3) and 5'-CAGAACCAGTCAGGCCCATCGGG-3' (SEQ ID NO:4). The Cas9 nickase coding plasmid was pX335-U6-Chimeric_BB-CBh-hSpCas9n-D10A (pX335) purchased from Addgene 42335. For HB9 reporter, the coding region of human MNs and pancreas homeobox 1 (MNX1; homeobox protein HB9) was analyzed, and the paired guide RNAs with the highest specificities and lowest off-target effects were selected. The sequences of paired guide RNAs at chromosome 7 were as follows: 5'-ACGCTGGCGCCGTTGCTGTAGGG-3' (SEQ ID NO:5) and 5'-AGGACGACTCGCCGCCCCCGCGG-3' (SEQ ID NO:6). For TDP43-M337V (chr1.11082475) correction, wild-type TDP43 was generated with an autonomous selection cassette, GFP and neomycin coding sequences driven by human elongation factor-1 alpha. For HB9 reporter (chr7:156797547-156802129), a 2A linker and GFP coding sequence were integrated at the C-terminus of the HB9 coding region. Drug selection was carried out by an autonomous selection cassette, neomycin coding sequences driven by human elongation factor-1 alpha. The knock-in cassette was inserted at the overhang created by Cas9 double nicking with 1 kb flanking homology arms to the locus.

NEAT1 Knockdown:

For shNEAT1-expressing vectors in virus system, oligonucleotides specifically targeting NEAT1 sequence were synthesized (Genedragon), cloned into the pLKO vector according to the standard annealing protocol provided by the RNAi core (Academia Sinica, Taiwan), and verified by sequencing. Targeting sequences are listed in following Table 2. Lentiviral particles carrying shNEAT1 were generated in HEK293T cells by transient transfection with lipofectamine and/or $CaCl_2$. The induced motor neurons were infected with lentivirus and then cultured in neuronal medium for 3 days for further experiments.

TABLE 2

Targeting sequences

| shNEAT1 | OLIGO SEQUENCE |
|---|---|
| shNEAT1a | CCGGGTGAGAAGTTGCTTAGAAACTTTCCCTCGAG GGAAAGTTTCTAAGCAACTTCTCAC TTTTT (SEQ ID NO: 1) |
| shNEAT1b | CCGGCTGGTATGTTGCTCTGTATGGTAAGCTCGAGCTTACCATACAGA GCAACATACCAGTTTTT (SEQ ID NO: 2) |
| shNEAT1c | GTGAGAAGTTGCTTAGAAACTTTCC (SEQ ID NO: 34) |
| shNEAT1d | CTGGTATGTTGCTCTGTATGGTAAG (SEQ ID NO: 35) | iPSCs were cultured in Rho Kinase (ROCK) inhibitor (Y27632) (Calbiochem) 24 hrs prior to transfection. Cells were co-transfected with 1.5 µg of gRNAs and HDR template as recommended based on manufacturing protocol of lipofectamine 3000 (Life Technology). Neomycin was treated 2 days post-transfection, and cell colonies were isolated after 10 days. To validate editing, PCR and Sanger sequencing were carried out. Whole genome sequencing analysis revealed the high specificity of gRNAs for TDP43-M337V (chr1.11082475) correction in iTDPs.

Measurement of Intact Cellular Respiration:

Intact cellular respiration was measured using Seahorse XF24 Extracellular Flux Analyzers (Seahorse Bioscience, North Billerica, Mass., USA) based on the manufacturer's protocol. MNs were plated at a density of 40,000 cells/well on matrigel (BD Biosciences)-coated XF24 tissue culture plates. Oxygen consumption rates (OCR) were measured under basal conditions to assess maximal oxidative capacity.

TUNEL Assay:

MNs were dissociated and seeded on matrigel-coated coverslips for TUNEL assay by using the DeadEnd™ Fluorometric TUNEL System kit or DeadEnd™ Colorimetric TUNEL System (Promega, Wis., USA). Apoptotic DNA fragments were visualized with catalytically-incorporated fluorescein-12-dUTP at the 3' end through recombinant Terminal Deoxynucleotidyl Transferase (rTdT).

Sequential Immunofluorescence and RNA Fluorescence In Situ Hybridization:

FISH analysis was performed for human NEAT using probe labeled with Quasar 570 Dye (Biosearch technologies, Petaluma, Calif., USA). Sequential immunofluorescence and FISH were performed sequentially based on the manufacturer's protocols. Briefly, cells were fixed with 4% paraformaldehyde for 10 mins, permeabilized in 0.1% Triton-X100 for 10 mins, and sequentially incubated with primary and secondary antibodies. Additional fixation for 10 mins was performed before RNA fluorescence in situ hybridization with 125 nM Quasar 570 conjugated NEAT1 probe at 37° C.

NEAT1 Pulldown Assay:

NEAT1 constructs were generated as previously described. In vitro transcription was labeled with biotin and carried out based on instruction of TranscriptAid T7 High Yield Transcription Kit (ThermoFisher). Purified transcripts were ready for pulldown. MNs were differentiated and lysed at day 27-28 with N-Mer Mamalian protein extraction regent (ThermoFisher). Two hundred microgram of cell lysate were used for pulldown based on instruction of Pierce™ Magnetic RNA-Protein Pull-Down Kit (ThermoFisher). The products were ready for immunoblotting.

Immunofluorescence:

For immunostaining iPSC motor neurons, cells were grown on matrigel-coated coverslips, and subjected to the following steps: fixation in 4% PFA, permeabilization in 0.2% Triton X-100 and blocking in 2% BSA. Primary antibodies were incubated 4° C. overnight (TDP43 and phospho(409/410)-TDP43, Proteintech 10782-2-AP and 22309-1-ap; TUJ1, COVACE PRB-435p; MAP2, Chemicon, AB5622; ChAT chemicon, AB144p; SMI32 COVANCE, SMI-32p; GFP, abcam ab13970 and Cleaved Caspase-3, Cell signaling 9661). Human ESCs and iPSCs were cultured on cover glass and fixed by incubating with 4% paraformaldehyde for 20 min at room temperature. Fixed cells were then washed with PBS and permeabilized using a non-ionic detergent (0.1% Triton X-100 and 0.2% Tween-20) in PBS for 40 min at RT. Permeabilized cells were blocked by incubating with 2% goat serum (Invitrogen) for 1 h, washed with PBS containing 0.01% Tween-20 (PBST), and incubated with primary antibody. Primary antibodies used included anti-PAX6 (Abcam; Ab5790), anti-NANOG (Abcam; Ab21624), anti-OCT4 (Millipore; MAB4401) (Santa Cruz, sc-9081), anti-TRA-1-60(Chemicon; MAB4360); anti-SSEA4 (Millipore, MAB43040). Cells were then washed with PBST and incubated with the appropriate fluorescein-conjugated secondary antibody. Stained samples were mounted using Vectashield H-1200 mounting media (Vector Laboratories), and images were captured using a fluorescence microscope (Leica). Positive signals were processed and counted using metamorph with a consistent intensity threshold.

Insoluble Protein Fraction:

Differentiated MNs were harvested at day 30 and lysed with M-PER mammalian protein extracting reagents (Thermo Fisher) supplied with protease inhibitor Cocktail (Sigma-Aldrich). After sonication with Bioruptor (ON: 30 seconds, OFF: 30 seconds, 10 times) (diagenode), samples were centrifuged at 16,000×g for 10 min at 4° C. The pellet was resuspended in 2x Sample buffer and sonicated with Bioruptor (ON: 30 sec, OFF: 30 sec, 30 times) and saved as insoluble fraction. The CRISPRa inducted NPCs were treated as above at the day 6 after transfection.

Neural Differentiation and CRISPRa:

Human ESCs H9 (WiCell, Madison, Wis.) were dissociated with 1 mg/ml dispase (ThermoFisher) and formed embryoid bodies (EBs) for 4 days in hES media (Dulbecco's modified Eagle's medium (DMEM)/F12, 20% knockout serum replacement, 1% non-essential amino acids, 2 mM L-glutamine, 100 mM 2-mercaptoethanol). Neural differentiation was induced in N2 media [DMEM/F12, N2 supplement, 1% non-essential amino acids, 2 mM L-glutamine and 20 ng/ml basic fibroblast growth factor (all purchased from Invitrogen)] for another 2 days. Neural spheres were transferred to new tissue-culture-treated dish for another 8 days. Then, neural progenitor cell (NPCs) were dissociated with TrypLE (Invitrogen) and maintained in matrigel coated dishes with motor neuron basal medium (MNBM) for further use.

CRISPRa (dCas9 activation) was based on dCas9 fused with effectors-VP64-P65-Rta (Sp-dCas9-VPR) (Addgene 63798). Based on CRISPR Design Tool upstream of NEAT1 transcription start site, eleven gRNAs were designed. The sequences of NEAT1 gRNAs are shown in Table 3. Cas9 nickase from px335 was deleted to generate px335-U6 for gRNA constructs. For NEAT1 activation in NPCs, 2.5 mg of Sp-dCas9-VPR and 0.5 mg of each gRNA were used for $1'10^6$. Cells were harvested day 3 post-transfection. Total RNA was extracted with TRizol (Invitrogen) for qPCR analysis of NEAT1 upregulation. The qPCR primer pairs for NEAT1 expression were designed around every 3 kb on NEAT1 and listed in Table 4.

TABLE 3

Efficiency of CRISPR-Cas9n Approaches for HB9::GFP
Summary of Targeting Efficiency of CRISPR/Cas9n Approaches for HB9::GFP

| Cell line | Additional Treatment | No. of clones analyzed | Precise targeting | | Targeting efficiency (%) |
|---|---|---|---|---|---|
| | | | Heterozygous | Homozygous | |
| CTLs and iTDP | 1 uM SCR7 | 32 | 3 | 6 | 28 |
| CTLs and iTDP | ——— | 15 | 5 | 1 | 40 |
| | 0.1 uM SCR7 | 13 | 2 | 2 | 30 |
| | 1 uM SCR7 | 19 | 1 | 3 | 21 |

TABLE 4 primers and gRNA lists

NEAT1 primers for qPCR

| | forward CRISPRA for NEAT1 | reverse |
|---|---|---|
| 1k | TTAGCGACAGGGAGGGATGC (SEQ ID NO: 7) | AGACCTAGTCTCCTTGCCAAGC (SEQ ID NO: 8) |
| 3k | ACCCTGAGGTGGGAGTTGTG (SEQ ID NO: 9) | CCAGTGCCAAGCTGCATACC (SEQ ID NO: 10) |
| 6k | TGTTGATACAGGAGCAGAGAGGTG (SEQ ID NO: 11) | CAACACCTCCTGTCGATCTCACC (SEQ ID NO: 12) |
| 8k | CCGTGGTGTGTGTTGTGGAATC (SEQ ID NO: 13) | CCATTCAGGAAACATCAGCCTGC (SEQ ID NO: 14) |
| 12k | GTCATGTGTCTGCTGGTGATGC (SEQ ID NO: 15) | TGCAATGCAGGCATAAGCAGAG (SEQ ID NO: 16) |
| 17k | TGGTGGCTCATGCCTGTAGTC (SEQ ID NO: 17) | AACTCTTGGCCTCAGATGATCCTC (SEQ ID NO: 18) |
| 19k | AGCCTGGGTGACAGAGTGAG (SEQ ID NO: 19) | ACAGGCCACTTCCTCAGATAACC (SEQ ID NO: 20) |
| 21k | TCGAGTGATGGCAGTTCCCAG (SEQ ID NO: 21) | TGGCCTAGTGGAAATGGTTCTCTG (SEQ ID NO: 22) |

| CRISPRa-NEAT1 gRNA sequence | NEAT1 Distance to TSS |
|---|---|
| AAAGTTGTGGCAAGTCCAGC (SEQ ID NO: 23) | −21 |
| AGCACTGTTAAAGAGAAGCG (SEQ ID NO: 24) | −202 |
| CGAAAGTCACGCGCGCCTCC (SEQ ID NO: 25) | −507 |
| CGCCCGACCTCAACAACATC (SEQ ID NO: 26) | −299 |
| CTCCCGTCGCCCACTCAAGA (SEQ ID NO: 27) | −370 |

TABLE 4-continued primers and gRNA lists

| | |
|---|---|
| GAATTTTCCAGATGTCCTGC (SEQ ID NO: 28) | -462 |
| GATACACTGGGGTCCTTGCG (SEQ ID NO: 29) | -180 |
| GGAGTCTCTCCGGGCAGGGT (SEQ ID NO: 30) | -128 |
| GGCCAGAGAAACCGCCTGTT (SEQ ID NO: 31) | -645 |
| GTCATCGGCCGAGCCCGACT (SEQ ID NO: 32) | -540 |
| GTCCCGTTGAGCAATGACCC (SEQ ID NO: 33) | -70 |

Cell Free System for Protein Aggregation:

Flag-TDP43 were inserted on pIVEX2.3 [36]. The flag-TDP43-M337V construct was modified on flag-TDP43 at 1006A>G by mutagenesis (KAPA HiFi, KAPABIOSYSTEM). For flag-TDP43 and flag-TDP43-M337V expression in eukaryotic cell-free system, plasmids were applied in rabbit reticulocyte lysate in vitro transcription/translation at 30° C. for 2 hrs with agitation (TNT T7 Quick-Coupled Transcription/Translation System, Promega). Additional 22 hrs were applied for self-aggregation of TDP43 and TDP43-M337V. Human NEAT1 constructs were generated in pcDNA3.1 backbone and purified (TranscriptAid T7 High Yield Transcription Kit, Thermo Fisher Scientific). For NEAT1 promoting protein aggregation, the purified RNAs were applied after expression of flag-TDP43 and flag-TDP43-M337V for another 22 hrs at 30° C. The mixtures were centrifuged at 16,000×g for 20 min to separate soluble (supernatant, denoted as S) and insoluble fraction (pellet, denoted as P) for western blot with anti-FLAG M2(F3165, Sigma). The insolubility was obtained by the equation S/(S+P).

TEM Immunuogold Staining:

The pellet from cell-free mixture were resuspended and diluted to 10 times volume with deionized water for later use. The fresh aliquot, 10 µL of each sample, was mounted on a glow-charged carbon-coated copper grid for 3 min and dried with a delicate wiper. Then, the grid was dipped in solution containing anti-FLAG M2 monoclonal antibody (1:5000) (Sigma) for an hour. For labeling of 12-nm-immunogold-linked antibody (1:20) (abcam), the grids were displayed on a sheet of parafilm for an hour. After wash with deionized water, the grids were staining with 2% uranyl acetate for 30 sec and ready for imaging. TEM images were recorded using a FEI Tecnai G2 TF20 TWIN electron microscope operated at 120 kV.

Figure 1D:
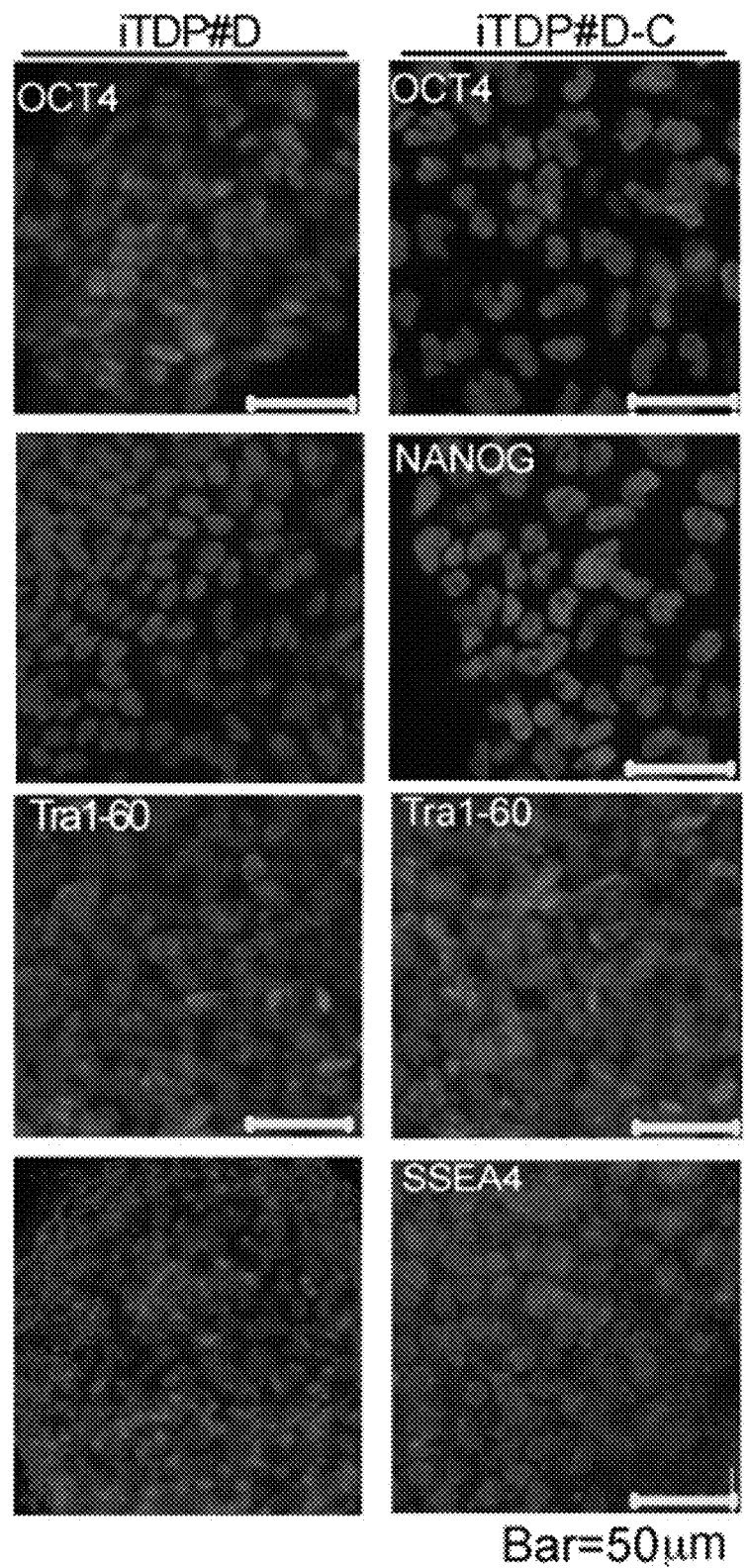

Example 1 Correction of TDP43-M337V in iPSCs Derived from Three ALS Patients We had harvested and identified dermal fibroblasts from three familial ALS patients carrying TDP43 heterozygous mutation at M337V denoted as iTDP #C, iTDP #D and iTDP #F. The iPSCs were derived by transducing four transcription factors (OCT4, SOX2, KLF4 and c-MYC) into dermal fibroblast derived from individual patients, and denoted as iTDP #1, iTDP #2 and iTDP #3. Patient profiles are described in Table 1. Validation of pluripotency were first performed by detecting endogenous pluripotent transcripts including OCT4, SOX2, KLF4 and c-MYC. To determine whether the ALS phenotypes were caused by TDP43-M337V, the CRISPR-Cas9 double nicking approach was used for correcting 1006G>A on the SNP allele. Targeting sites of the paired-guide RNAs (gRNA) are shown in FIG. 1A. Considering gRNA off-target effects and targeting efficiency, Cas9 nickase and homologous recombination were adapted along with selection markers. Sanger sequencing had been carried out for validation of TDP43-M337V mutation in individual iTDP and its corrected line, denoted as iTDP #1-C and iTDP #2-C and iTDP #3-C based on the parental iTDPs (FIG. 1B). Our efficiency for correcting iTDPs was up to 40.3% with additional treatment for improving HDR including RS-1 and SCR-7 (Table 5). By whole genome sequencing, we observed up to 157 positions of SNP/INDEL among the 381 potential off-target sites of gRNA-A and B comparing each iTDP to reference genome sequence. In our approach, the SNP/INDEL were eliminated to less than 2 between iTDP #1 v.s. iTDP #2-C, iTDP #2 v.s. iTDP #2-C, and iTDP #3 v.s. iTDP #3-C (FIG. 1C). Pluripotency markers were used to characterize sub-clones of iTDP #1-C and iTDP #2-C and iTDP #3-C by cell morphology and immunofluorescence staining including OCT4, NANOG, Tra1-60 and SSEA4 (FIG. 1 D and FIGS. 9A to 9C).

In advances of both CRISPR-Cas9 double nicking and iPSC technologies, we generated three pairs of iPSCs for exploring familial ALS caused by TDP43-M337V heterozygous mutation. This approach provides a set of iPSCs for future investigation of TDP43-M337V caused ALS pathogenesis with minimum genetic variation. We also successfully improved the efficiency of CRISPR-Cas9 on iPSC with combination of drug selection and small molecules for improving HDR.

TABLE 5

Efficiency of CRISPR-Cas9n Approaches for TDP43M337V
Efficiency of CRISPR/Cas9n Approaches for TDP43-M337V

| iTDP Lines | Treatment | No. of clones analyzed | M337V (G > A) | Targeting efficiency (%) |
|---|---|---|---|---|
| iTDP#1 | 0.1 µM SCR7* | 27 | 4 | 14.8 |
| iTDP#1 | 0.2 µM SCR7* | 35 | 2 | 5.7 |
| iTDP#1 | 0.5 µM SCR7* | 24 | 9 | 17.6 |
| iTDP#1 | 1 µM SCR7* | 16 | 4 | 29.4 |
| iTDP#2 | 1 µM SCR7* | 28 | 1 | 3.6 |

TABLE 5-continued

Efficiency of CRISPR-Cas9n Approaches for TDP43M337V
Efficiency of CRISPR/Cas9n Approaches for TDP43-M337V

| iTDP Lines | Treatment | No. of clones analyzed | M337V (G > A) | Targeting efficiency (%) |
|---|---|---|---|---|
| iTDP#2 | 1 µM SCR7* 10 µM RS-1* | 32 | 6 | 40.6 |
| iTDP#3 | 1 µM SCR7* 10 µM RS-1* | 32 | 2 | 6.3 |

Figure 3A:
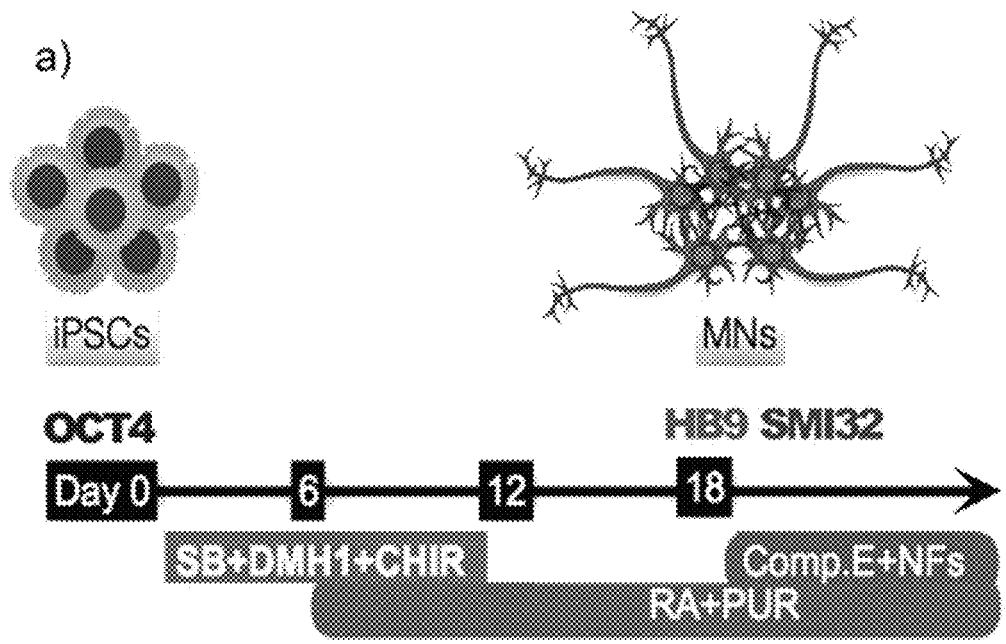
FIGS. 3A to 3F shows that CRISPR-Cas9n mediates Knock-in for MN reporting lines.
Figure 3B:
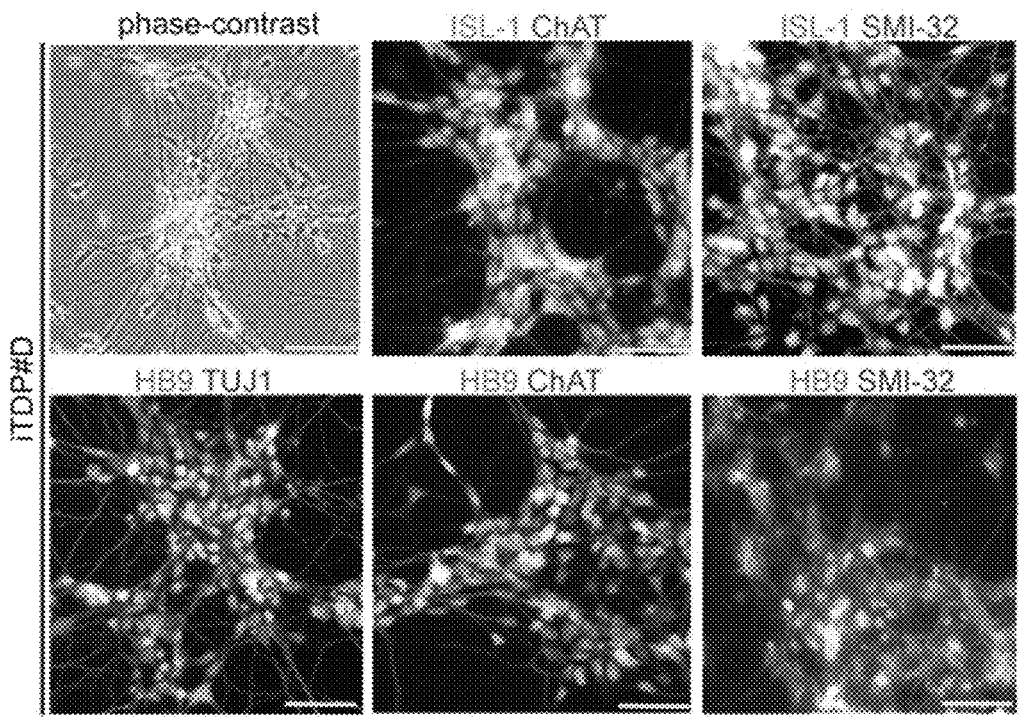
Figure 3C:
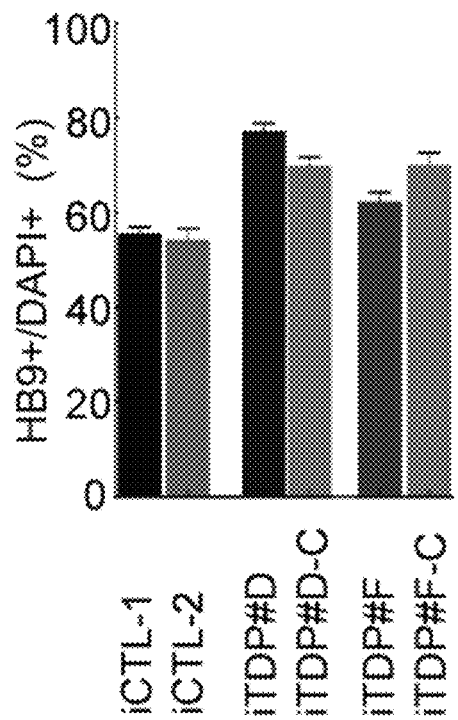

*SCR7: (5,6-bis((E)-benzylideneamino)-2-thioxo-2,3-dihydropyrimidin-4(1H)-one), inhibits NHEJ in a Ligase IV-dependent manner
*RS-1: (3-((benzylamino)sulfonyl]-4-bromo-N-(4-bromophenyl)benzamide), enhances HDR through stimulation of RAD51 in HDR complex Example 2 Recapitulation of TDP43-M337V Caused TDP43 Pathology and Neuron Degeneration in iTDP Derived Motor Neurons Motor neuron differentiation was carried out based on the reported protocol with minor adjustment (FIG. 3A). Significant amounts of MNs were elevated by increasing retinoic acid (RA) and purmorphamine (SHH signaling agonist) from 0.5 µM to 1 µM since day 12 (FIG. 10). In FIG. 3B, the MN validation was performed by immunostaining including MAP2, TUJ1, ISL-1, HB9, SMI32 and ChAT. The capabilities of generating HB9+ MNs were not affected by TDP43-M337V by comparing counted cell numbers between each pair derived MNs (FIG. 3C).

Figure 2A:
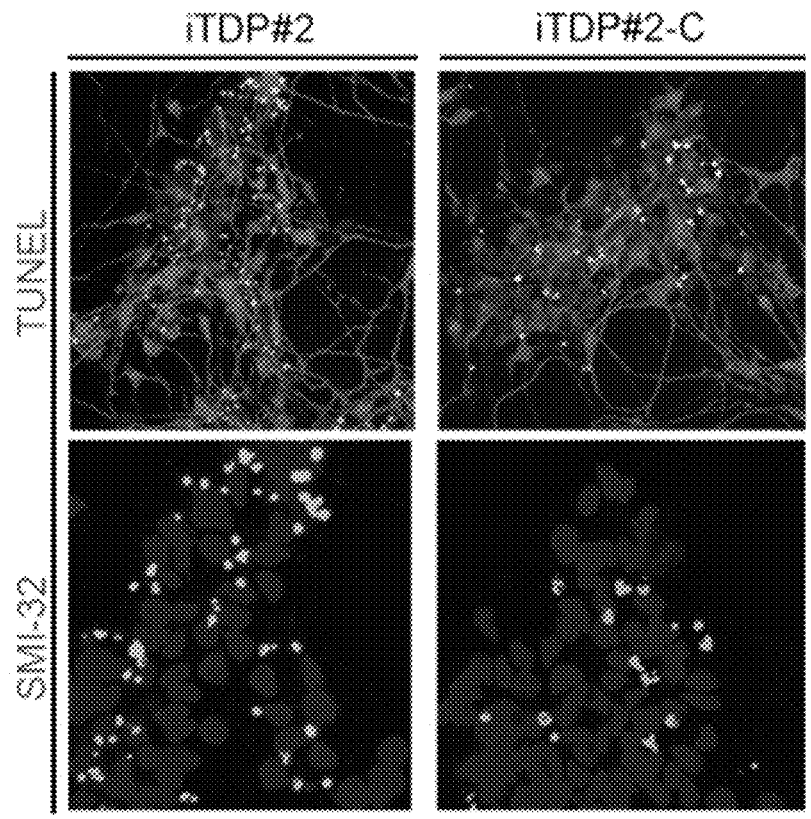
FIGS. 2A to 2K shows that recapitulation of TDP43-M337V causes pathogenesis and neuron degeneration in MNs derived from iTDPs. TUNEL analysis of MN death. Scale bar: 50 um.
Figure 2B:
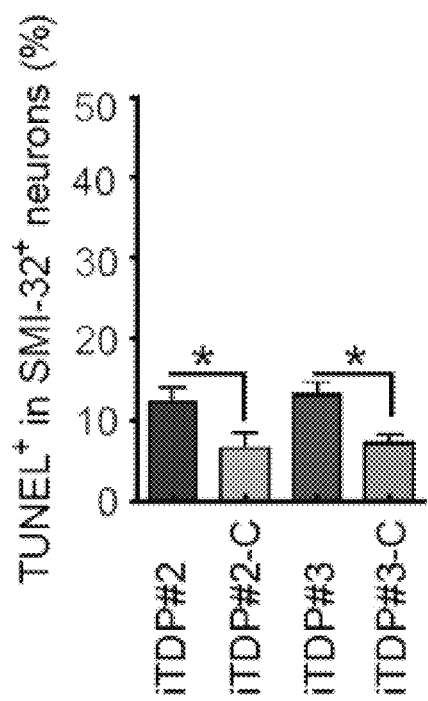
Figure 2C:
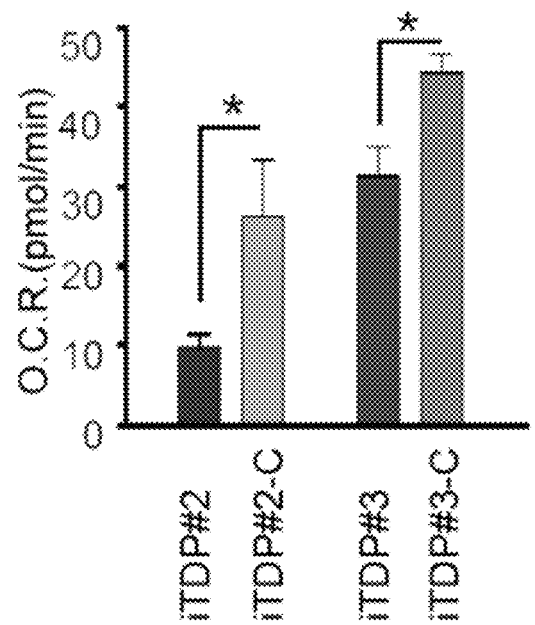

Pathogenic mutations in TDP-43 were reported in familial ALS patients. The defined pathology in ALS includes apoptosis, mitochondria dysfunction and TDP43 mislocalization/oligomerization/aggregation. To determine whether TDP43-M337V manifest ALS phenotypes under our culture conditions, we first investigated the lethal MN degeneration. At day 25 of in vitro MN induction, TUNEL assay was carried out for the degenerative MNs. In SMI32+ MNs, the TUNEL cells were about 15% and 17% in iTDP #2 and iTDP #3 respectively. In iTDP #2-C and iTDP #3-C, TUNEL cells were decreased to 8% and 7.3% respectively (FIGS. 2A and 2B). For mitochondrial function, TDP43-M337V also contributed to lowering oxygen consumption rates in iTDP #2 and iTDP #3 related to iTDP #2-C and iTDP #3-C separately (FIG. 2C). Our data suggested TDP43-M337V as a cause of decreasing MN survival rates, and heterozygous mutation of TDP43-M337V dramatically drove MNs toward to mitochondrial dysfunction and cell death.

Figure 2D:
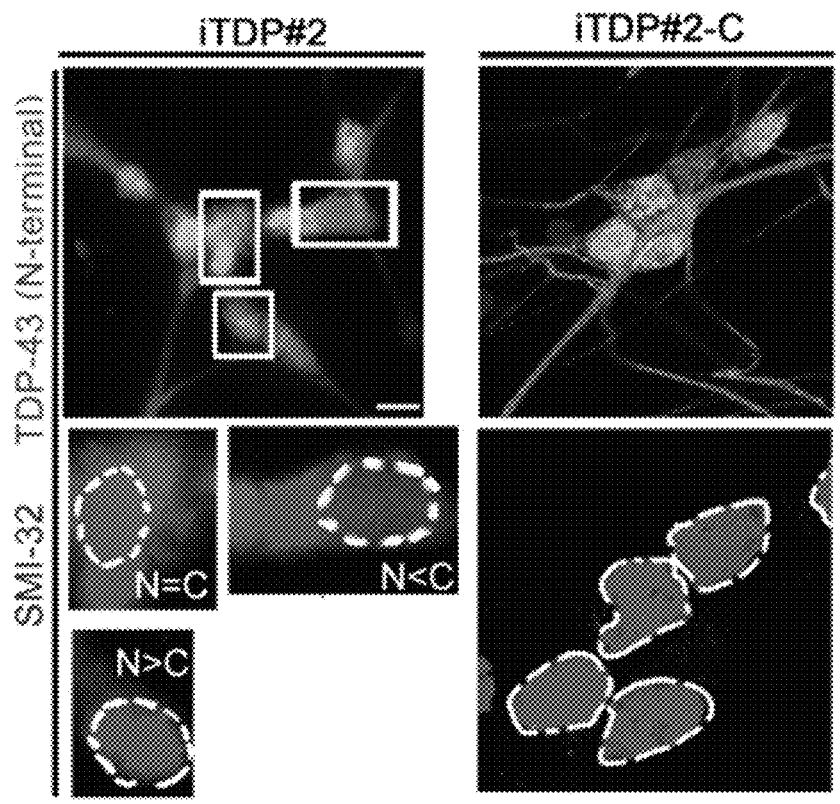
Figure 2E:
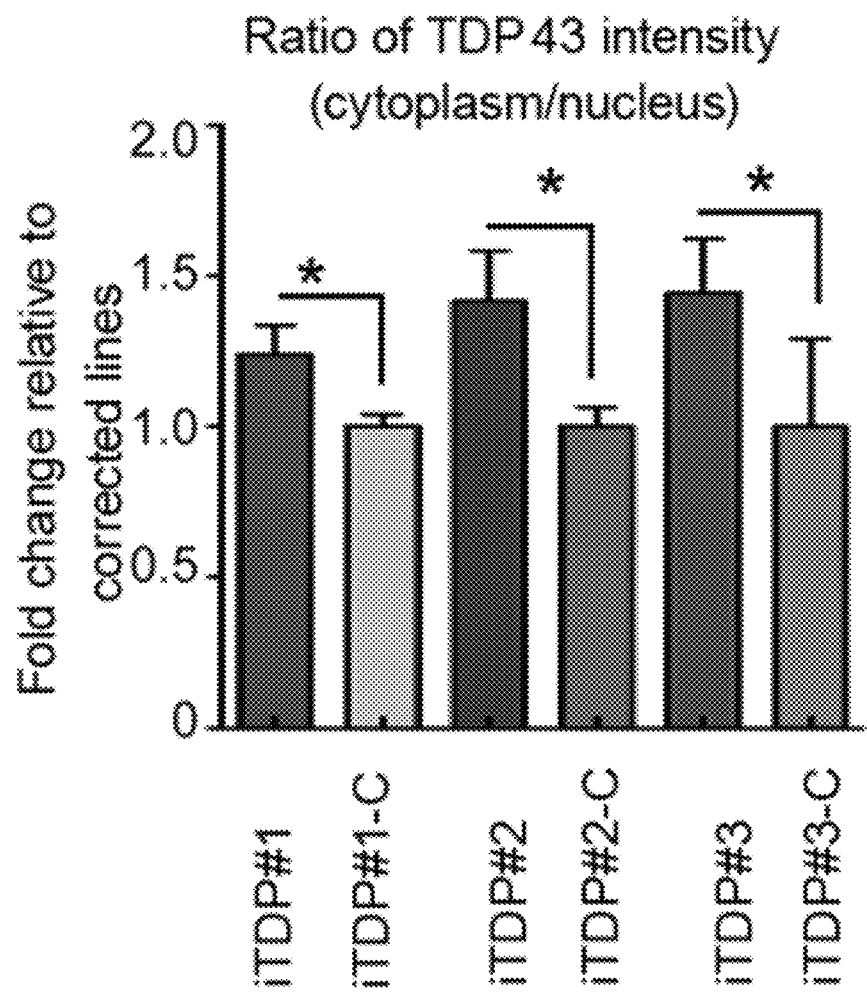
Figure 2F:
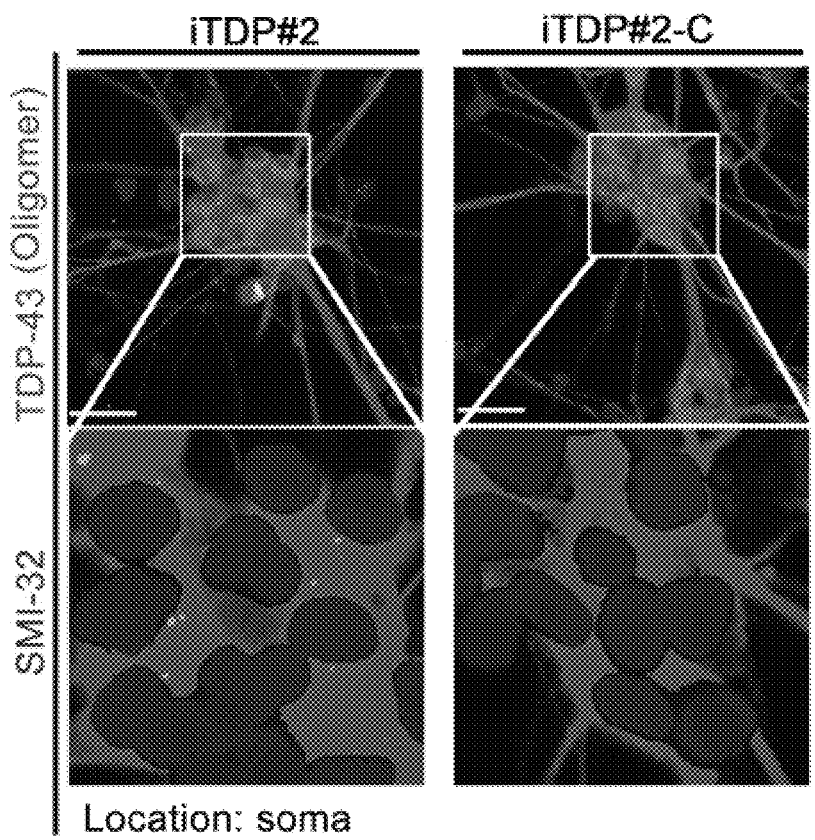
Figure 2G:
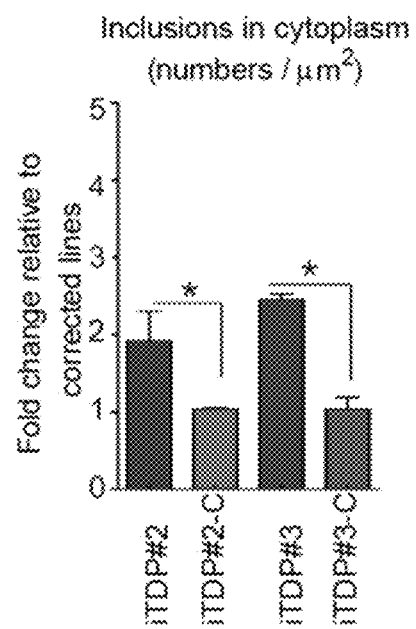
Figure 2H:
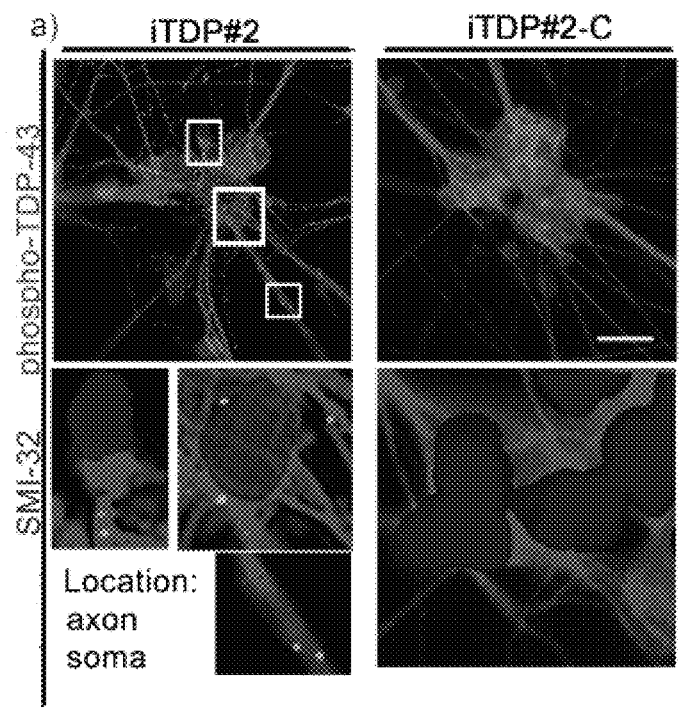
Figure 2I:
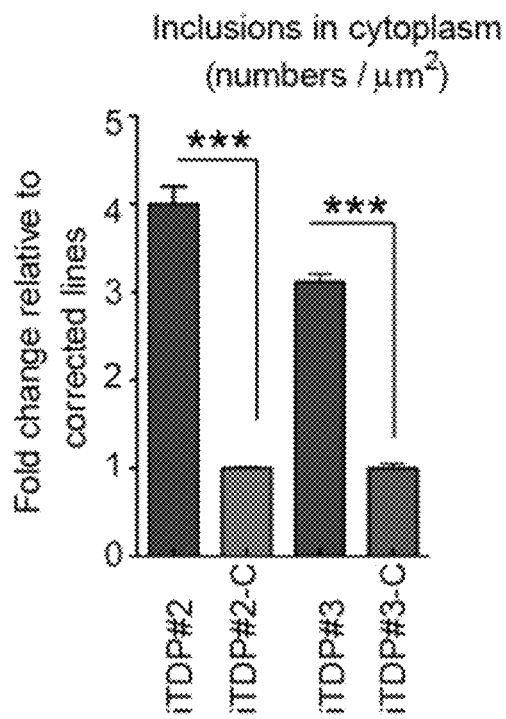

TDP43 mislocalization/oligomerization/aggregation, the hallmark of ALS, has been reported as detergent resistant and cytoplasmic preinclusions in ALS postmortem tissues. In Frontotemporal Lobar Degeneration-TDP postmortem tissues, TDP-43 oligomers were detected. In FIGS. 2D and 2E, the subcellular distribution of TDP43 revealed that TDP43-M337V led to TDP43 mislocalization by counting relative cell numbers containing cytoplasmic TDP43 signal in SMI-32+ neurons at day 28. As representative images in FIG. 2D, there were three types of TDP43 mislocalization observed in our system based on relative TDP43 intensity in nucleus and cytoplasm from one MN. However, nuclear TDP43 expression was the majority of TDP43 distribution in MNs derived from corrected iPSCs including iTDP #1-C, iTDP #2-C and iTDP #3-C. In FIGS. 2F and 2G, the cytoplasmic spherical TDP43 oligomers were also identified and elevated in iTDP #2 and iTDP #3 related to iTDP #2-C and iTDP #3-C. Interestingly, TDP43 oligomers were mainly located in neuronal soma of iTDP #2 and iTDP #3 derived MNs. The abnormal TDP43 inclusions were also observed in our system by immunostaining with phosphor (409/410)-TDP43 (FIGS. 2H and 2I). The increased numbers of inclusion were identified in MNs derived from iTDP #2 and iTDP #3 related to iTDP #2-C and iTDP #3-C. The inclusions were distributed in neuronal soma, axon and distal axons. In order to identify progress of TDP43 proteinopathy, we had measured the TDP43 events observed above and observed at different time points of MN induction. In day 28, the TDP43 mislocalization and oligomers were significantly increased in iTDP #3 derived MNs relative to iTDP #3-C-derived MNs. The phosphor (409/410)-TDP43 was significantly increased at day 34.

Figure 2J:
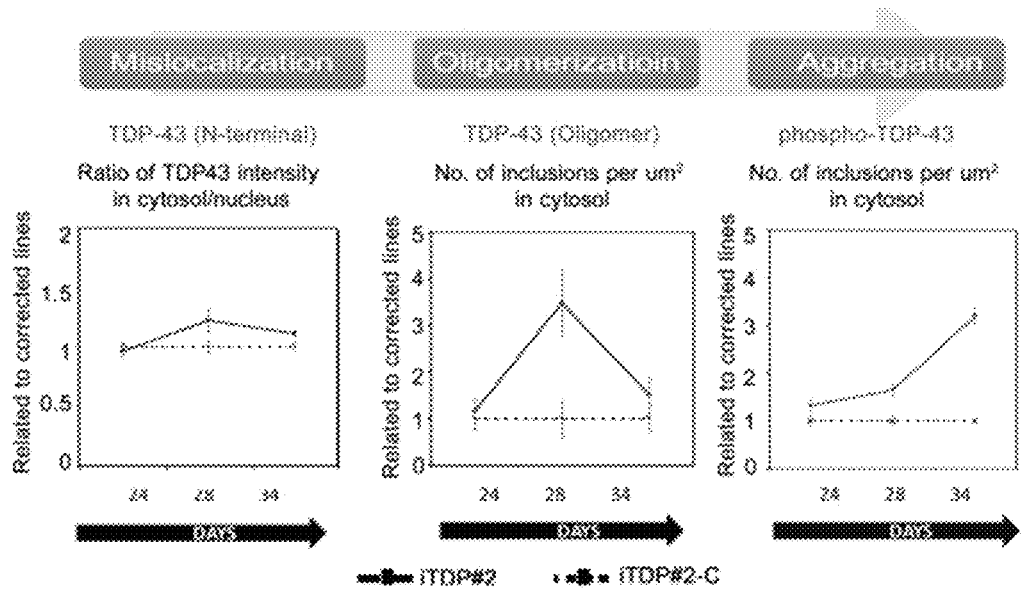
Figure 2K:
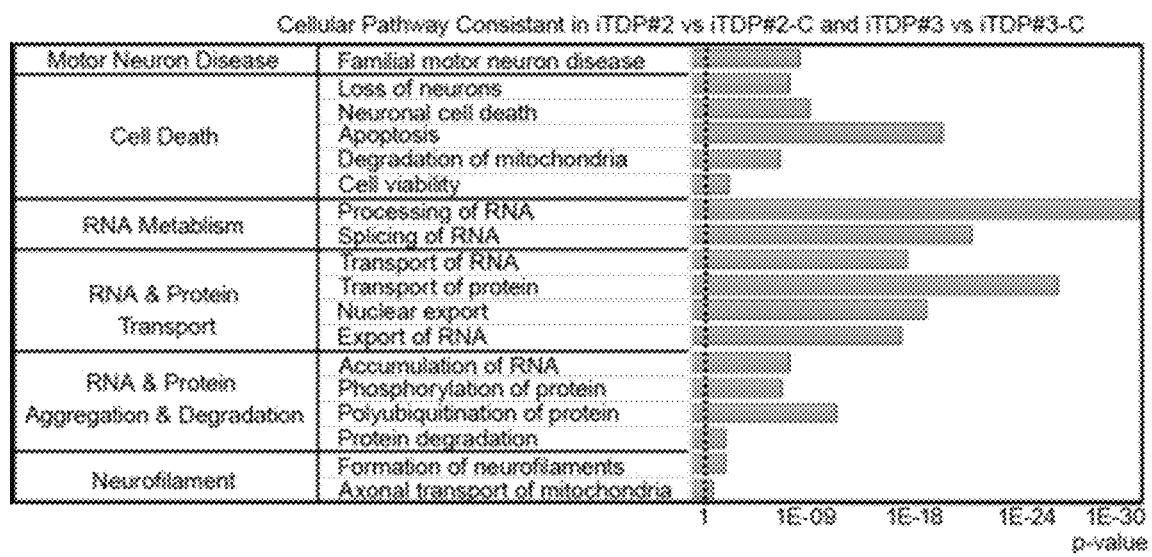
Figure 3D:
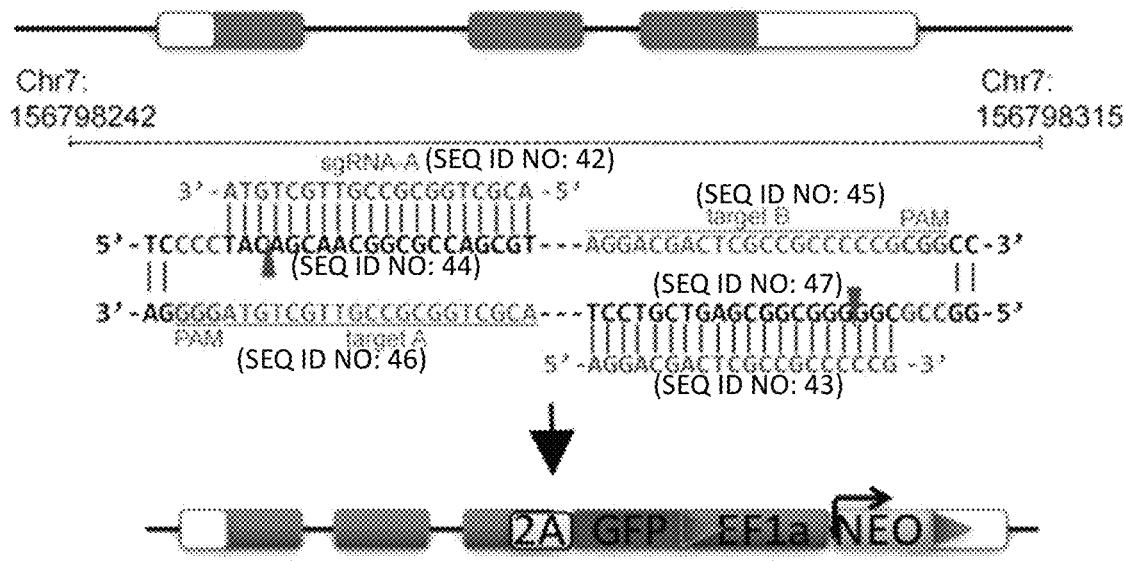
Figure 3E:
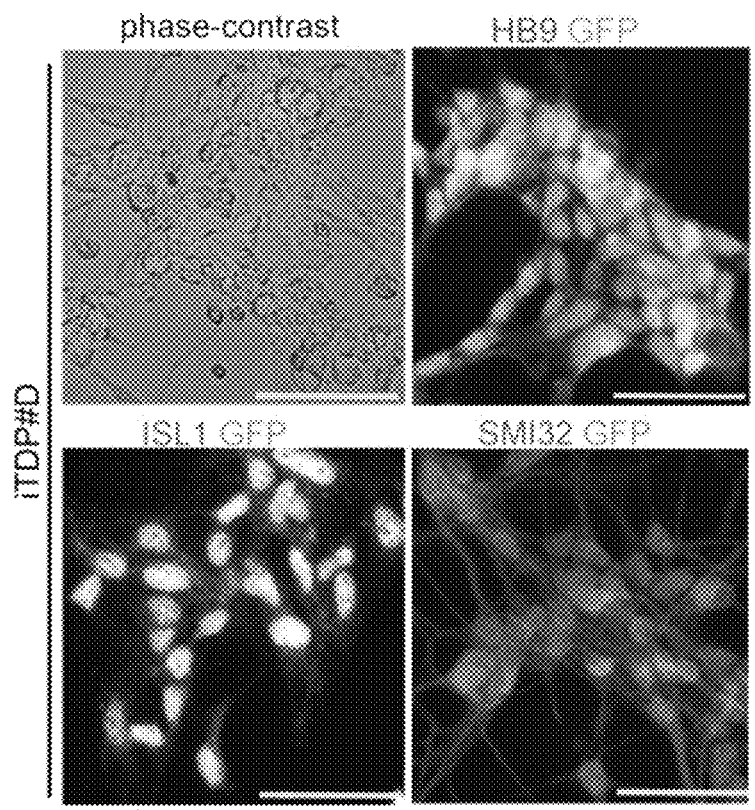
Figure 3F:
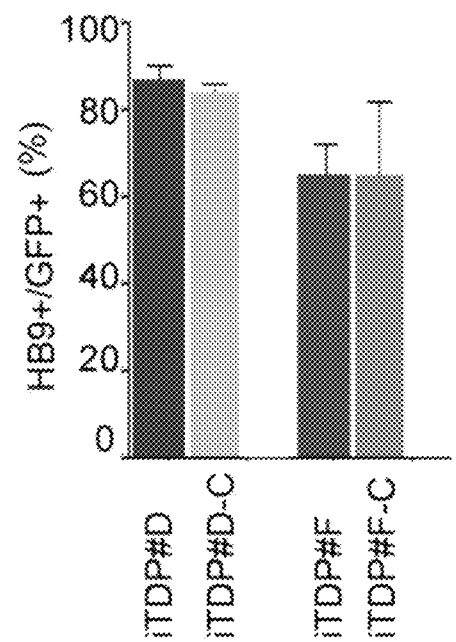

As we and others have described, the purity of iPSC-derived motor neurons is variable. For better understanding MN specific disease mechanism, CRISPR-Cas9 had successfully been applied for generating HB9 reporter driven by endogenously transcriptional regions (FIG. 3D). We targeted HB9 C-terminal coding region at chromosome 7 by Cas9 double nicking creating a 5'overhang. HDR occurred simultaneously for precise insertion by introducing a donor plasmid bearing a 2A-GFP with autonomous selection cassette. Precise insertion was validated by PCR and followed Sanger sequencing (FIGS. 11A to 11C). The efficiency of precise insertion and reporting MNs were up to 40% (Table 4). FIGS. 3E and 3F indicates HB9::GFP+ cells also expressed the MN markers validated by immunostaining with MN markers ISL-1, HB9 and SMI-32. Quantitatively, above 60% of HB9+ cells were expressed in GFP cells. Our GFP-tagged HB9 cells accurately reports MN generation during in vitro differentiation. Therefore, FACS was performed for HB9+ MNs isolation by visualized GFP and applied for microarray analysis for exploring HB9+ MN specific mechanism. A global analysis of transcription array was performed, and the other ALS associated cellular pathways were also recapitulated in our platforms including RNA metabolism, RNA/protein transport and neurofilament associated pathways, which we did not explore in this study (FIG. 2J).

Taken together, we have recapitulated ALS phenotypic effects in our platform. Although we can't reveal the other causes at this point, MN degeneration kicked off was due to TDP43-M337V heterozygous mutation. Importantly, the TDP43 mislocalization, oligomerization and aggregation were significantly increased and observed in iTDPs derived MNs. A single protein-altering difference was revealed in TDP43-M337V where the mutant was on C terminal low complexity domain. Our model provides a proper platform for studying the downstream mechanisms caused by TDP43-M337V and potential for ALS drug development.

Example 3 Endogenous NEAT1 Enhances Cytoplasmic TDP43 Aggregation and Motor Neuron Death TDP-43 is known as RNA binding protein involving RNA processing, metabolism and so on. In global microarray analysis of lncRNA expression from purified HB9+MNs, aberrations in certain lncRNAs were identified between iTDP #3 and iTDP #3-C. As seen in FIGS. 4A to 4C, several distinct lncRNAs were identified in iTDP #3 derived MNs. Validation by quantitative RT-PCR, we have identified that the transcript of NEAT1 were upregulated in three iTDPs. RNA in situ hybridization were performed to validate NEAT1 expression pattern in SMI32+ MNs. In iTDP #2 and iTDP #3 compared with iTDP #2-C and iTDP #3-C separately, the relatively higher intensity of NEAT1 was observed. Similar results were observed in the proportion of cells with NEAT1. Interestingly, cytoplasmic NEAT1 was also observed in MNs derived from iTDP #1, iTDP #2 and iTDP #3; however, the majority of NEAT1 were in the nucleus after genetic correction (FIGS. 4D to 4G).

To gain further insight of NEAT1 in ALS pathogenesis, the lentivirus-based shRNAs were introduced to knock down NEAT1 expression in iTDP #2 and iTDP #3 derived MNs. FIGS. 5A to 5C indicates NEAT1 knockdown efficiency in transcript and cells proportion (SMI32$^+$). As shown in FIGS. 5D and 5E, the progression of MN degeneration was delayed in NEAT1 knockdown MNs derived from iTDP #2 and iTDP #3. The death rates of iTDP #2-shNEAT1 and iTDP #2-C are similar. Same rescuing abilities from NEAT1 knockdown was also observed in iTDP #3 derived MNs by counting cell numbers of TUNEL$^+$ in knockdown MNs. To explore whether NEAT1 associated cell death was involved in TDP43 pathology, shNEAT1 in iTDP derived MNs were explored. As shown in literatures, cytoplasmic TDP43 aggregation and inclusion are increased in ALS (Brettschneider, J., et al., *Stages of pTDP-43 pathology in amyotrophic lateral sclerosis. Ann Neurol*, 2013. 74(1): p. 20-38). In FIGS. 2A to 2K, we also recapitulated phenotypes of TDP43 oligomers and inclusions (phospho-TDP43) in MNs derived from iTDP #2 and iTDP #3. In the NEAT1 knockdown MNs derived from iTDP #2 and iTDP #3, the decreased cell numbers with TDP43 inclusions were observed (FIGS. 5F and 5G). This rescuing result were not observed in TDP43 oligomers (FIGS. 12A and 12B). In literatures (Tollervey, J. R., et al., *Characterizing the RNA targets and position-dependent splicing regulation by TDP-43. Nat Neurosci*, 2011. 14(4): p. 452-8) and our NEAT1 pulldown assay in FIGS. 8A to 8D, the interaction between TDP43 and NEAT1 were observed. In the MNs derived from iTDP #2 and iTDP #3, TDP43 inclusions were recruited to cytoplasm in the presence of NEAT1 foci. The colocalization of TDP43 and NEAT1 in cytoplasm was up to 70%. However, this interaction was not observed in NEAT1 knockdown MN derived iTDP #2 and iTDP #3 (FIGS. 5H and 5I). Taken together, these results demonstrate that NEAT1 was involved in TDP43 aggregation and neuron degeneration in iTDP #2 and iTDP #3 derived MNs. Reducing NEAT1 by short hairpin RNA rescued TDP43 aggregation and further degeneration.

To investigate the role of NEAT1 in promoting TDP43 aggregations, the CRISPRa technology was adopted for enhancing NEAT1 expression in vitro differentiated NPCs derived from human embryonic stem cells H9. Demonstration of the dCas9 and gRNAs for NEAT1 activation is shown in FIG. 6A. A mixture of gRNAs targeting upstream of NEAT1 transcription start site (TSS) was used along with dCas9 fused with VP64-p65-Rta for recruiting transcription activators. The validation of NEAT1 enhancement performed by quantitative RT-PCR and RNA in situ hybridization related to dCas9 only NPCs (FIGS. 6B and 6C). Due to the length of NEAT1_2, eight sites on NEAT1 were amplified for transcriptional confirmation of full length NEAT1_2. The probes for RNA in situ hybridization was designed for NEAT1_2 nts 3800-11700. As shown in FIG. 6C, RNA counts both of NEAT1_1 and NEAT1_2 were increased with the presence of gRNAs. To visualize the association between NEAT1 and TDP43 aggregation, immunostaining of TDP43 was performed in transfected NPCs. In the CRISPRa-NEAT1 cells, TUNEL$^+$ cells were increased from 10 to 25% (FIG. 6D). Cleaved caspase 3 was also observed in NEAT1 upregulated NPCs (FIG. 6E). Moreover, TDP43 inclusions detected by phospho-TDP43 were associated and colocalized with NEAT1 in cytoplasm (FIG. 6F). Altogether, these data suggest that NEAT1 promoted cytoplasmic TDP43 aggregation and cell death in neuronal cells.

In postmortem and induced MNs derived from ALS patient, detergent-resistant TDP43 has been reported (Neumann, M., et al., *Ubiquitinated TDP-43 in frontotemporal lobar degeneration and amyotrophic lateral sclerosis. Science*, 2006. 314(5796): p. 130-3). To analyze biochemical properties in which NEAT1 may be involved, detergent-insoluble fractions were immunoblotted for TDP43. The amount of insoluble TDP43 were elevated in the MNs derived from iTDP #2 and iTDP #3. TDP43 insolubility was rescued in NEAT1 knockdown MNs derived from iTDP #2 and iTDP #3 (FIG. 7A). The CRISPRa-NEAT1 was also used to confirm NEAT1 engaged TDP43 insolubility.

Altogether, NEAT1 may play a vital role in mediating ALS pathogenesis including cell death, TDP43 aggregating and inclusions. Knockdown of NEAT1 with short hairpin RNA can rescue the above ALS pathology while enhancement of NEAT1 expression recruits. Therefore, targeting NEAT1 may disrupt TDP43 aggregation and further cell death.

Example 4 NEAT1 Directly Interacts and Promotes Both TDP43 and TDP43-M337V Aggregation We first performed NEAT1 pulldown to test the interaction between NEAT1 and TDP43 (FIG. 8A). Next, we examined whether NEAT1 directly interact with wild-type TDP43 and/or TDP43-M337V. A cell-free system was used to produce TDP43 or TDP43-M337V protein by in vitro transcription/translation in rabbit reticulocyte lysate systems (Huang, Y. C., et al., *Inhibition of TDP-43 aggregation by nucleic acid binding. PLoS One*, 2013. 8(5): p. e64002). The insolubility of recombinant TDP43 and TDP43-M337V were promoted by increasing input plasmids, which has been shown as self-seeding ability of pathological TDP43 in a concentration-dependent manner (FIG. 8B). Next, NEAT1 RNA were co-incubated with TDP43 or TDP43-M337V. Intriguingly, NEAT1 promoted both insolubility of TDP43 and TDP43-M337V in a concentration-dependent manner (FIG. 8C). With TEM immunogoldstaining in the insoluble pellet, we observed that NEAT1 nanostructure was co-aggregated with TDP43 or TDP43-M337V (immunogold particles). Thus, NEAT1 may be provided as a scaffold for increasing insolubility of both TDP43 and TDP43-M337V, which enhances the interaction of low-complexity domain of TDP43 and TDP43-M337V for pathological aggregates formation.

Overall, these data suggest that NEAT1 directly interacted with TDP43 or TDP43-M337V and resulted in protein aggregation. Targeting NEAT1 would provide a potential role for disrupting TDP43 associated aggregates and further prevents motor neurons degeneration.

What is claimed is:

1. A method of reducing neurodegeneration associated with TDP43 aggregation and/or TDP43 associated aggregation in a subject suffering from neurodegeneration associated with TDP43 aggregation and/or TDP43 associated aggregation, comprising administering to the subject a nucleic acid that knocks down, downregulates or inhibit Nuclear Paraspeckle Assembly Transcript 1 (NEAT1) expression; or an nucleic acid inhibiting, silencing or downregulating LncRNA NEAT1.

2. The method of claim 1, wherein the knockdown of NEAT1 or LncRNA NEAT1 results in treating a motor neuron degeneration disease associated with TDP43 aggregation.

3. The method of claim 1, wherein NEAT1 or LncRNA NEAT1 is knockdown by SEQ ID NO: 1, 2, 34 or 35 or a 2'-O-methoxy modification thereof.

4. A method of treating a motor neuron degeneration disease associated with TDP43 aggregation in a subject suffering from the motor neuron degeneration disease associated with TDP43 aggregation, comprising administering to the subject a nucleic acid that knocks down, downregulates or inhibit NEAT1 expression; or a nucleic acid inhibiting, silencing or downregulating LncRNA NEAT1.

5. The method of claim 4, wherein the nucleic acid is a short nucleic acid molecule.

6. The method of claim 5, wherein the short nucleic acid molecule is a short interfering RNA (siRNA), double stranded RNA (dsRNA), micro RNA (miRNA), short hairpin RNA (shRNA), or interfering DNA (DNAi) molecules.

7. The method of claim 5, wherein the short nucleic acid molecule comprises a nucleotide sequence of SEQ ID NO: 1, 2, 34 or 35, or a 2'-O-methoxy modification thereof.

8. The method of claim 4, wherein the a motor neuron degeneration disease associated with TDP43 aggregation is amyotrophic lateral sclerosis (ALS) or spinal muscular atrophies (SMA).

9. The method of claim 8, wherein the ALS is familial ALS or sporadic ALS.

10. A short nucleic acid molecule, comprising a nucleotide sequence consisting of SEQ ID NO: 1 or 2, wherein the short nucleic acid molecule comprises a 2'-O-methoxy modification.

* * * * *

SEQUENCE LISTING

<160> NUMBER OF SEQ ID NOS: 47

<210> SEQ ID NO 1
<211> LENGTH: 65
<212> TYPE: DNA
<213> ORGANISM: Artificial Sequence
<220> FEATURE:
<223> OTHER INFORMATION: oligonucleotides specifically targeting NEAT1
      sequence

<400> SEQUENCE: 1
ccgggtgaga agttgcttag aaactttccc tcgagggaaa gtttctaagc aacttctcac    60
ttttt                                                               65

<210> SEQ ID NO 2
<211> LENGTH: 65
<212> TYPE: DNA
<213> ORGANISM: Artificial Sequence
<220> FEATURE:
<223> OTHER INFORMATION: oligonucleotides specifically targeting NEAT1
      sequence

<400> SEQUENCE: 2
ccggctggta tgttgctctg tatggtaagc tcgagcttac catacagagc aacataccag    60
ttttt                                                               65

<210> SEQ ID NO 3
<211> LENGTH: 20
<212> TYPE: DNA
<213> ORGANISM: Artificial Sequence
<220> FEATURE:
<223> OTHER INFORMATION: paired guide RNAs at chromosome 1

<400> SEQUENCE: 3
aactgctctg tagtgctgcc                                               20

<210> SEQ ID NO 4
<211> LENGTH: 23
<212> TYPE: DNA
<213> ORGANISM: Artificial Sequence
<220> FEATURE:
<223> OTHER INFORMATION: paired guide RNAs at chromosome 1

<400> SEQUENCE: 4
cagaaccagt caggcccatc ggg                                           23

<210> SEQ ID NO 5
<211> LENGTH: 23
<212> TYPE: DNA
<213> ORGANISM: Artificial Sequence
<220> FEATURE:
<223> OTHER INFORMATION: paired guide RNAs at chromosome 7

<400> SEQUENCE: 5
acgctggcgc cgttgctgta ggg                                           23

<210> SEQ ID NO 6
<211> LENGTH: 23
<212> TYPE: DNA
<213> ORGANISM: Artificial Sequence
<220> FEATURE:
<223> OTHER INFORMATION: paired guide RNAs at chromosome 7

<400> SEQUENCE: 6
aggacgactc gccgcccccg cgg                                           23

```
<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
ttagcgacag ggagggatgc                                              20

<210> SEQ ID NO 8
<211> LENGTH: 22
<212> TYPE: DNA
<213> ORGANISM: Artificial Sequence
<220> FEATURE:
<223> OTHER INFORMATION: synthetic primer

<400> SEQUENCE: 8
agacctagtc tccttgccaa gc                                           22

<210> SEQ ID NO 9
<211> LENGTH: 20
<212> TYPE: DNA
<213> ORGANISM: Artificial Sequence
<220> FEATURE:
<223> OTHER INFORMATION: synthetic primer

<400> SEQUENCE: 9
accctgaggt gggagttgtg                                              20

<210> SEQ ID NO 10
<211> LENGTH: 20
<212> TYPE: DNA
<213> ORGANISM: Artificial Sequence
<220> FEATURE:
<223> OTHER INFORMATION: synthetic primer

<400> SEQUENCE: 10
ccagtgccaa gctgcatacc                                              20

<210> SEQ ID NO 11
<211> LENGTH: 24
<212> TYPE: DNA
<213> ORGANISM: Artificial Sequence
<220> FEATURE:
<223> OTHER INFORMATION: synthetic primer

<400> SEQUENCE: 11
tgttgataca ggagcagaga ggtg                                         24

<210> SEQ ID NO 12
<211> LENGTH: 23
<212> TYPE: DNA
<213> ORGANISM: Artificial Sequence
<220> FEATURE:
<223> OTHER INFORMATION: synthetic primer

<400> SEQUENCE: 12
caacacctcc tgtcgatctc acc                                          23

<210> SEQ ID NO 13
<211> LENGTH: 22
<212> TYPE: DNA
<213> ORGANISM: Artificial Sequence
<220> FEATURE:
<223> OTHER INFORMATION: synthetic primer
```

```
<400> SEQUENCE: 13
ccgtggtgtg tgttgtggaa tc                                          22

<210> SEQ ID NO 14
<211> LENGTH: 23
<212> TYPE: DNA
<213> ORGANISM: Artificial Sequence
<220> FEATURE:
<223> OTHER INFORMATION: synthetic primer

<400> SEQUENCE: 14
ccattcagga aacatcagcc tgc                                         23

<210> SEQ ID NO 15
<211> LENGTH: 22
<212> TYPE: DNA
<213> ORGANISM: Artificial Sequence
<220> FEATURE:
<223> OTHER INFORMATION: synthetic primer

<400> SEQUENCE: 15
gtcatgtgtc tgctggtgat gc                                          22

<210> SEQ ID NO 16
<211> LENGTH: 22
<212> TYPE: DNA
<213> ORGANISM: Artificial Sequence
<220> FEATURE:
<223> OTHER INFORMATION: synthetic primer

<400> SEQUENCE: 16
tgcaatgcag gcataagcag ag                                          22

<210> SEQ ID NO 17
<211> LENGTH: 21
<212> TYPE: DNA
<213> ORGANISM: Artificial Sequence
<220> FEATURE:
<223> OTHER INFORMATION: synthetic primer

<400> SEQUENCE: 17
tggtggctca tgcctgtagt c                                           21

<210> SEQ ID NO 18
<211> LENGTH: 24
<212> TYPE: DNA
<213> ORGANISM: Artificial Sequence
<220> FEATURE:
<223> OTHER INFORMATION: synthetic primer

<400> SEQUENCE: 18
aactcttggc ctcagatgat cctc                                        24

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
agcctgggtg acagagtgag                                             20
```

```
<210> SEQ ID NO 20
<211> LENGTH: 23
<212> TYPE: DNA
<213> ORGANISM: Artificial Sequence
<220> FEATURE:
<223> OTHER INFORMATION: synthetic primer

<400> SEQUENCE: 20
acaggccact tcctcagata acc                                             23

<210> SEQ ID NO 21
<211> LENGTH: 21
<212> TYPE: DNA
<213> ORGANISM: Artificial Sequence
<220> FEATURE:
<223> OTHER INFORMATION: synthetic primer

<400> SEQUENCE: 21
tcgagtgatg gcagttccca g                                               21

<210> SEQ ID NO 22
<211> LENGTH: 24
<212> TYPE: DNA
<213> ORGANISM: Artificial Sequence
<220> FEATURE:
<223> OTHER INFORMATION: synthetic primer

<400> SEQUENCE: 22
tggcctagtg gaaatggttc tctg                                            24

<210> SEQ ID NO 23
<211> LENGTH: 20
<212> TYPE: DNA
<213> ORGANISM: Artificial Sequence
<220> FEATURE:
<223> OTHER INFORMATION: gRNA

<400> SEQUENCE: 23
aaagttgtgg caagtccagc                                                 20

<210> SEQ ID NO 24
<211> LENGTH: 20
<212> TYPE: DNA
<213> ORGANISM: Artificial Sequence
<220> FEATURE:
<223> OTHER INFORMATION: gRNA

<400> SEQUENCE: 24
agcactgtta aagagaagcg                                                 20

<210> SEQ ID NO 25
<211> LENGTH: 20
<212> TYPE: DNA
<213> ORGANISM: Artificial Sequence
<220> FEATURE:
<223> OTHER INFORMATION: gRNA

<400> SEQUENCE: 25
cgaaagtcac gcgcgcctcc                                                 20

<210> SEQ ID NO 26
<211> LENGTH: 20
<212> TYPE: DNA
<213> ORGANISM: Artificial Sequence
<220> FEATURE:
<223> OTHER INFORMATION: gRNA
```

<400> SEQUENCE: 26
cgcccgacct caacaacatc                                               20

<210> SEQ ID NO 27
<211> LENGTH: 20
<212> TYPE: DNA
<213> ORGANISM: Artificial Sequence
<220> FEATURE:
<223> OTHER INFORMATION: gRNA

<400> SEQUENCE: 27
ctcccgtcgc ccactcaaga                                               20

<210> SEQ ID NO 28
<211> LENGTH: 20
<212> TYPE: DNA
<213> ORGANISM: Artificial Sequence
<220> FEATURE:
<223> OTHER INFORMATION: gRNA

<400> SEQUENCE: 28
gaattttcca gatgtcctgc                                               20

<210> SEQ ID NO 29
<211> LENGTH: 20
<212> TYPE: DNA
<213> ORGANISM: Artificial Sequence
<220> FEATURE:
<223> OTHER INFORMATION: gRNA

<400> SEQUENCE: 29
gatacactgg ggtccttgcg                                               20

<210> SEQ ID NO 30
<211> LENGTH: 20
<212> TYPE: DNA
<213> ORGANISM: Artificial Sequence
<220> FEATURE:
<223> OTHER INFORMATION: gRNA

<400> SEQUENCE: 30
ggagtctctc cgggcagggt                                               20

<210> SEQ ID NO 31
<211> LENGTH: 20
<212> TYPE: DNA
<213> ORGANISM: Artificial Sequence
<220> FEATURE:
<223> OTHER INFORMATION: gRNA

<400> SEQUENCE: 31
ggccagagaa accgcctgtt                                               20

<210> SEQ ID NO 32
<211> LENGTH: 20
<212> TYPE: DNA
<213> ORGANISM: Artificial Sequence
<220> FEATURE:
<223> OTHER INFORMATION: gRNA

<400> SEQUENCE: 32
gtcatcggcc gagcccgact                                               20

```
<210> SEQ ID NO 33
<211> LENGTH: 20
<212> TYPE: DNA
<213> ORGANISM: Artificial Sequence
<220> FEATURE:
<223> OTHER INFORMATION: gRNA

<400> SEQUENCE: 33
gtcccgttga gcaatgaccc                                               20

<210> SEQ ID NO 34
<211> LENGTH: 25
<212> TYPE: DNA
<213> ORGANISM: Artificial Sequence
<220> FEATURE:
<223> OTHER INFORMATION: oligonucleotides specifically targeting NEAT1
      sequence

<400> SEQUENCE: 34
gtgagaagtt gcttagaaac tttcc                                         25

<210> SEQ ID NO 35
<211> LENGTH: 25
<212> TYPE: DNA
<213> ORGANISM: Artificial Sequence
<220> FEATURE:
<223> OTHER INFORMATION: oligonucleotides specifically targeting NEAT1
      sequence

<400> SEQUENCE: 35
ctggtatgtt gctctgtatg gtaag                                         25

<210> SEQ ID NO 36
<211> LENGTH: 20
<212> TYPE: DNA
<213> ORGANISM: Artificial Sequence
<220> FEATURE:
<223> OTHER INFORMATION: paired guide RNAs at chromosome 1

<400> SEQUENCE: 36
cagaaccagt caggcccatc                                               20

<210> SEQ ID NO 37
<211> LENGTH: 25
<212> TYPE: DNA
<213> ORGANISM: Homo sapiens

<400> SEQUENCE: 37
gcccaggcag cactacagag cagtt                                         25

<210> SEQ ID NO 38
<211> LENGTH: 25
<212> TYPE: DNA
<213> ORGANISM: Homo sapiens

<400> SEQUENCE: 38
cagaaccagt caggcccatc gggta                                         25

<210> SEQ ID NO 39
<211> LENGTH: 25
<212> TYPE: DNA
<213> ORGANISM: Homo sapiens

<400> SEQUENCE: 39
aactgctctg tagtgctgcc tgggc                                         25
```

<210> SEQ ID NO 40
<211> LENGTH: 25
<212> TYPE: DNA
<213> ORGANISM: Homo sapiens

<400> SEQUENCE: 40
tacccgatgg gcctgactgg ttctg                                    25

<210> SEQ ID NO 41
<211> LENGTH: 18
<212> TYPE: DNA
<213> ORGANISM: Homo sapiens

<400> SEQUENCE: 41
gggtatgatg ggcatgtt                                            18

<210> SEQ ID NO 42
<211> LENGTH: 20
<212> TYPE: DNA
<213> ORGANISM: Artificial Sequence
<220> FEATURE:
<223> OTHER INFORMATION: paired guide RNAs at chromosome 7

<400> SEQUENCE: 42
acgctggcgc cgttgctgta                                          20

<210> SEQ ID NO 43
<211> LENGTH: 20
<212> TYPE: DNA
<213> ORGANISM: Artificial Sequence
<220> FEATURE:
<223> OTHER INFORMATION: paired guide RNAs at chromosome 7

<400> SEQUENCE: 43
aggacgactc gccgcccccg                                          20

<210> SEQ ID NO 44
<211> LENGTH: 25
<212> TYPE: DNA
<213> ORGANISM: Homo sapiens

<400> SEQUENCE: 44
tcccctacag caacggcgcc agcgt                                    25

<210> SEQ ID NO 45
<211> LENGTH: 25
<212> TYPE: DNA
<213> ORGANISM: Homo sapiens

<400> SEQUENCE: 45
aggacgactc gccgcccccg cggcc                                    25

<210> SEQ ID NO 46
<211> LENGTH: 25
<212> TYPE: DNA
<213> ORGANISM: Homo sapiens

<400> SEQUENCE: 46
acgctggcgc cgttgctgta ggggga                                   25

<210> SEQ ID NO 47
<211> LENGTH: 25
<212> TYPE: DNA
<213> ORGANISM: Homo sapiens -continued

```
<400> SEQUENCE: 47
ggccgcgggg gcggcgagtc gtcct                                              25
```